(12) United States Patent
Kosai et al.

(10) Patent No.: US 7,803,780 B2
(45) Date of Patent: Sep. 28, 2010

(54) DRUG FOR PREVENTING OR TREATING HEART DISEASES COMPRISING CD9 GENE

(75) Inventors: Kenichiro Kosai, Fukuoka (JP); Hiroaki Ushikoshi, Gifu (JP)

(73) Assignee: Nagoya Industrial Science Research Institute, Aichi (JP)

( * ) Notice: Subject to any disclaimer, the term of this patent is extended or adjusted under 35 U.S.C. 154(b) by 689 days.

(21) Appl. No.: 10/584,109

(22) PCT Filed: Dec. 24, 2004

(86) PCT No.: PCT/JP2004/019774
§ 371 (c)(1),
(2), (4) Date: Jun. 22, 2006

(87) PCT Pub. No.: WO2005/063302
PCT Pub. Date: Jul. 14, 2005

(65) Prior Publication Data
US 2007/0161584 A1 Jul. 12, 2007

(30) Foreign Application Priority Data
Dec. 26, 2003 (JP) .............................. 2003-432279

(51) Int. Cl.
A61K 31/70 (2006.01)
A61K 48/00 (2006.01)
C12N 15/63 (2006.01)
A01K 67/00 (2006.01)
(52) U.S. Cl. .......................... 514/44; 424/93.2; 435/455
(58) Field of Classification Search ........................ None
See application file for complete search history.

(56) References Cited

U.S. PATENT DOCUMENTS 6,638,502 B1 * 10/2003 Li et al. ...................... 424/93.2
7,060,433 B1 * 6/2006 Kinsella ........................ 435/6

OTHER PUBLICATIONS

Murayama et al 1: J Cell Physiol. 216(1):135-43, 2008.*
Raper, Surgery, 137(5):487-492, 2005.*
Kimmelman, BMJ, 220:79-82, 2003.*
Juengst, BMJ, 326:1410-1411, 2003.*
Wolf, Nat. Biotechnol. 20:768-769, 2002.*
Rosenberg et al, Science 287:1751, 2000.*
Donsante et al, Science, 317:477, 2007.*
Couzin et al, Science 307:1028, 2005.*
Touchette, Nat. Med. 2(1):7-8, 1996.*
Ushikoshi et al. Membrane protein CD9 regulates hypertrophy and heart failure via EGFR signaling in vitro and in vivo. Circulation, Supplement III, vol. 110, p. 8, 2004.*
Miyake et al. Suppression of pulmonary metastasis using adenovirally motility related protein-1 (MRP-1/CD9) gene delivery. Oncogene 19:5221-5226, 2000.*
Fujino et al. enhanced expression of heparin-binding EGF-like growth factor and its receptor in hypertrophied left ventricle of spontaneously hypertensive rats. Cardiovascular Res. 38:365-374, 1998.*
Tanaka et al. A role of heparin-binding epidermal growth factor-like growth factor in cardiac remodeling after myocardial infarction. Biochem. Biophys. Res. Commun. 297:375-381, 2002.*
Romano et al. Latest Developments in gene transfer technology: Achievements, perspectives, and controversies over therapeutic applications. Stem Cells 18:19-39, 2000.*
Verma et al. Gene therapy: Twenty-first century medicine. Annu. Revi. Biochem. 74:711-738, 2005.*
Gardlik et al. Vectors and delivery systems in gene therapy. Med. Sci. Monit. 11:RA110-121, 2005.*
Goncalves, M. A concise peer into the background, initial thoughts and practices of human gene therapy. BioEssays 27:506-517, 2005.*
Definition of "Cardiac catheterization" by American Heart Association, http://wwww.americanheart.org, 2010, pp. 1-3.*
Berditchevski, F., "Complexes of Tetraspanins with Integrins: More than Meets the Eye", *Journal of Cell Science*, vol. 114, pp. 4143-4151, 2001.
Dominguez-Jimenez, C. et al., "Involvement of α3 Integrin/Tetraspanin Complexes in the Angiogenic Response Induced by Angiotensin II", *FASEB Journal*, vol. 15, pp. 1457-1459, 2001.
Hashida, H. et al., "Clinical Significance of Transmembrane 4 Superfamily in Colon Cancer", *British journal of Cancer*, vol. 89, pp. 158-167, 2003.
Higashiyama, S. et al., "The Membrane Protein CD9/DRAP 27 Potentiates the Juxtacrine Growth Factor Activity of the Membrane-anchored Heparin-binding EGF-like Growth Factor", *The journal of Cell Biology*, vol. 128, pp. 929-938, 1995.
Iwamoto, R and Mekada E., "Heparin-binding EGF-like Growth Factor: A Juxtacrine Growth Factor", *Cytokine & Growth Factor Reviews*, vol. 11, pp. 335-344, 2000.
Iwamoto, R. et al., "Heparin-binding EGF-like Growth Factor and ErbB Signaling is Essential for Heart Function", *PNAS*, vol. 100, No. 6, pp. 3221-3226, 2003.
Jennings, L. K. et al., "The Activation of Human Platelets Mediated by Anti-human Platelet p24/CD9 Monoclonal Antibodies", *The Journal of Biological Chemistry*, vol. 265, No. 7, pp. 3815-3822, 1990.
Kirkland, G. et al., "Heparin-Binding EGF-Like Growth Factor mRNA Is Upregulated in the Peri-Infarct Region of the Remnant Kidney Model: In Vitro Evidence Suggests a Regulatory Role in Myofibroblast Transformation", *Journal of the American Society of Nephrology*, vol. 9, pp. 1464-1473, 1998.

(Continued)

*Primary Examiner*—Quang Nguyen
(74) *Attorney, Agent, or Firm*—Occhiuti Rohlicek & Tsao LLP

(57) ABSTRACT

A drug for preventing or treating heart diseases which comprises an expression vector containing CD9 gene as the active ingredient. In the present invention, the term "heart diseases" means diseases causative of heart failure, ischemic heart diseases, cardiomyopathy, hypertensive heart diseases, valvular disease, congenital heart diseases, mayocarditis, arrhythmia and diseases associated with cardiac hypertrophy and/or tachycardia. In the present invention, the expression vector is a viral vector or a non-viral vector. A method for preventing or treating heart diseases which comprises expressing the CD9 gene in the heart. In the present invention, the prevention or the treatment is carried out by a gene therapy of transferring the CD9 gene. In the gene therapy, use is made of a drug comprising an expression vector containing the CD9 gene as the active ingredient.

12 Claims, 23 Drawing Sheets

OTHER PUBLICATIONS

Klein-Soyer, C. et al. "CD9 Participates in Endothelial Cell Migration During In Vitro Wound Repair", *Arterioscler. Thromb. Vasc Biol.*, vol. 20, pp. 360-369, 2000.

Maecker, H. T. et al., "The Tetraspanin Superfamily: Molecular Facilitators", *The FASEB Journal*, vol. 11, pp. 428-442, 1997.

Masellis-Smith, A. et al., "Anti-CD9 Monoclonal Antibodies Induce Homotypic Adhesion of PRE-B Cell Lines by a Novel Mechanism", *The Journal of Immunology*, vol. 144, No. 5, pp. 1607-1613, 1990.

Miyado, K. et al., "Requirements of CD9 on the Egg Plasma Membrane for fertilization", *Science*, vol. 287, pp. 321-324, 2000.

Miyagawa, J.-i. et al., "Localization of Heparin-binding EGF-like Growth Factor in the Smooth Muscle Cells and Macrophages of Human Atherosclerotic Plaques", *J. Clin. Invest.*, vol. 95, pp. 404-411, 1995.

Morimoto, C. et al., "Epidermal Growth Factor: EGF (Heparin-binding EGF-like Growth Factor: HB-EGF)", *Clinical Endocrinology*, vol. 51, No. 12, 1137-1143, 2003.

Nakagawa, T. et al., "Amino-terminal Processing of Cell Surface Heparin-binding Epidermal Growth Factor-like Growth Factor Up-regulates Its Juxtacrine but Not its Paracrine Growth Factor Activity", *The Journal of Biological Chemistry*, vol. 271, No. 48, pp. 30858-30863, 1996.

Nakamura, K. et al., "Importance of the Major Extracellular Domain of CD9 and the Epidermal Growth Factor (EGF)-like Domain of Heparin-binding EGF-like Growth Factor for Up-regulation of Binding and Activity", *The Journal of Biological Chemistry*, vol. 275, No. 24, pp. 18284-18290, 2000.

Nakamura, Y. et al., "Immunohistochemical Distribution of CD9, Heparin Binding Epidermal Growth Factor-like Growth Factor, and Integrin $\alpha 3\beta 1$ in Normal Human Tissues", *The Journal of Histochemistry & Cytochemistry*, vol. 49, No. 4, pp. 439-444, 2001.

Nakata, A. et al., "Localization of Heparin-Binding Epidermal Growth Factor-Like Growth Factor in Human Coronary Arteries", *Circulation*, vol. 94, pp. 2778-2786, 1996.

Nishida, M. et al., "Localization of CD9, an Enhancer Protein for Proheparin-Binding Epidermal Growth Factor-Like Growth Factor, in Human Atherosclerotic Plaques", *Arterioscler Thromb Vasc Biol.*, vol. 20, pp. 1236-1243, 2000.

Takemura, T. et al., "Coexpression of CD9 Augments the Ability of Membrane-bound Heparin-binding Epidermal Growth Factor-like Growth Factor (pro HB-EGF) to Preserve Renal Epihelial Cell Viability", *Kidney International*, vol. 55, pp. 71-81, 1999.

Shah, Bukhtiar H. and Catt, Kevin J., "A central role of EFG receptor transactivation in angiotensin II-induced cardiac hypertrophy", Trends in Pharmacological Sciences, vol. 24, No. 5, pp. 239-244, abstract, 2003.

Hiroaki Ushikoshi et al., CD9 gene therapy inhibits cardiac hypertrophy and tachycardia, and attenuates the remopdeling after myocardial infarction in mice, Molecular Therapy, vol. 11, Supplement 1, pp. 359-360, 2005.

* cited by examiner

DRUG FOR PREVENTING OR TREATING HEART DISEASES COMPRISING CD9 GENE

CROSS-REFERENCE TO RELATED APPLICATIONS

This application is the National Stage of International Application No. PCT/JP2004/019774, filed on Dec. 24, 2004, which claims the benefit of Japanese Application Serial No. 0315360, filed on Dec. 24, 2003. The contents of both applications are hereby incorporated by reference in their entirety.

TECHNICAL FIELD

The present invention relates to a drug for preventing or treating heart diseases, more specifically, to a drug which is used for gene therapy and prevents or treats heart diseases by transferring a CD9 gene into heart.

BACKGROUND ART

Heart diseases such as myocardial infarction, cardiomypathy, arrhythmia, heart failure and the like are one of three major causes for death in Japan, generating a significant problem in medical care. Conventionally, drugs such as a diuretic, β-blocker, ACE inhibitor, calcium antagonist and the like are used for treatment of heart diseases, however, these drugs do not radically treat heart diseases.

CD9 is a membrane protein having a molecular weight of 27 kDa classified into one of transmembrane 4-times type protein super family (TM4SF). Regarding the action of CD9 in an organism, there are reports that it is a cell-specific marker derived from pre B (Masellis-Smith A et al; J Immunol. 144 15, 1607-1613, 1990), that it expresses in various cells irrespective of hematopoietic cells or non-hematopoietic cells (Maecker H. T et al.; FASEB J. 11, 428-442, 1997, Berditchevski F; J Cell Sci. 114, 4143-4151, 2001), that it relates to aggregation and differentiation of pre B cells (Masellis-Smith A et al; J Immunol. 144, 1607-1613, 1990), that it relates to activation of platelets (Jennings L K et al.; J Biol Chem. 265, 3815-3822, 1990), that it relates to survival and adhesion of various cells typically including cancer cells (Hashida H, et al.: Br J Cancer., 89: 158-67, 2003) , that it is a membrane protein indispensable for fertilization (Miyado K et al. ; Science 287, 321-324, 2000), that it causes association of a plurality of proteins in a cell membrane, acts as a molecule for coordinating and promoting a mutual action between proteins, and relates to phenomena of injury healing such as cell adhesion, proliferation, differentiation, immune, hemostatis and the like (Berditchevski F; J Cell Sci. 114, 4143-4151, 2001, Klein-Soyer C et al; Arterioscler Thromb Vasc Biol. 20, 360-3).

On the other hand, there is also a report regarding a relation between CD9 and HB-EGF (heparin binding growth factor). For example, there are reports on formation of a complex with HB-EGF or integrin α3β1 (Nakamura Y, et al: J Histochem Cytochem 49: 439-444, 2001), regulation of an activity as a juxtacrine factor of proHB-EGF as a precursor of HB-EGF (Higashiyama S., et al, : J. Cell Biol. 128, 929-938.1995, Iwamoto R, Mekada E: Cytokine & Growth Factor Reviews. 11: 335-344, 2000), and possibility of representation of variety of an activity of HB-EGF by relating to a process of processing of HB-EGF (Nakagawa T et al; J Biol Chem. 271, 30858-30863, 1996, Nakamura K et al; J Biol Chem. 275, 18284-18290, 2000). There are also reports that kidney epithelial cells also are improved in survival by co-expression of HB-EGF and CD9 in an ischemic disorder model (Takamura T et al; Kidney Int. 55, 71-81, 1999), that, in a process of arteriosclerosis, HB-EGF is expressed in normal aorta (Miyagawa J et al; J Clin Invest. 95, 404-411, 1995) and coronary (Nakata A et al; Circulation 94, 2778-2786, 1996), on the other and, CD9 expresses in arteriosclerosis lesion and some inner membrane smooth muscle cells, and co-expression of CD-9 and proHB-EGF promotes proliferation of smooth muscle cells by proHB-EGF (Nishida M et al; Arterioscler Thromb Vasc Biol. 20, 1236-1243, 2000), thus, CD9 is possibly an important molecule for regulating an activity of HB-GF assisting a balance of proliferation and transformation of fibroblasts in a process of arteriosclerosis and tissue repair (Kirkland G et al; J Am Soc Nephrol. 9, 1464-73, 1998). Further, the present inventors have a finding that excess expression of HB-EGF in a myocardial infarction model animal promotes compensatory hypertrophy of a myocardial cell, while promotes proliferation of myofibroblasts and enhances fibering, thereby, promoting decrease in a cardiac function, that is, HB-EGF is a central factor playing an important role in progressing of pathology.

As described above, there are a lot of reports on the action of CD9 and a relation of CD9 and HB-EGF, however, there is no report on a fact that CD9 suppresses cardiac hypertrophy, or suppresses tachycardia.

DISCLOSURE OF THE INVENTION

The present invention has an object of providing a drug which radically prevents or treats heart diseases. Another object is to provide a method for radically preventing or treating heart diseases.

The present invention relates to a drug for preventing or treating heart diseases, containing an expression vector containing a CD9 gene as the active ingredient. In the present invention, the heart diseases include diseases causative of heart failure, ischemic heart diseases, cardiomyopathy, hypertensive heart diseases, valvular disease, congenital heart diseases, mayocarditis, arrhythmia and diseases associated with arrhythmia, cardiac hypertrophy and/or tachycardia. The cardiac hypertrophy or tachycardia is caused by at least one of HB-EGF (heparin binding epidermal growth factor), HGF (hepatocyte growth factor) or angiotensin 2.

In the above-mentioned present invention, the expression vector is a viral vector or a non-viral vector.

The present invention also relates to a method for preventing or treating heart diseases, containing expressing a CD9 gene in heart. In this invention, the heart diseases include diseases causative of heart failure, ischemic heart diseases, cardiomyopathy, hypertensive heart diseases, valvular disease, congenital heart diseases, mayocarditis, arrhythmia and diseases associated with cardiac hypertrophy and/or tachycardia.

In this invention, the prevention or treatment may be carried out by a gene therapy of transferring a CD9 gene, or administration of an expression inducing substance for expressing endogenous CD9. Further, the gene therapy may use a drug containing an expression vector containing a CD9 gene as the active ingredient.

The CD9 gene used in the drug of the present invention means a gene capable of expressing CD9. The CD9 gene may be a gene in which its gene sequence is partially deleted, substituted, inserted or, other base is added, providing a polypeptide to be expressed has substantially the same effect as CD9. As the CD9 gene, a human CD9 gene described in Strausberg R. L. et al; Proc. Natl. Acd. Sci. U.S.A. 99, (26) 16899-16903, 2002 is exemplified (Gene Bank, accession No. is AAH11988, messenger RNA No. is BC011988).

The expression vector containing a CD9 gene includes virus vector, non-virus vector, plasmid and the like. Examples of the virus vector include adenovirus, adeno-associated virus, retrovirus, herpesvirus, herpes simplex virus, lentivirus, Sendai virus, poxvirus, poliovirus, symbis virus, vaccinia virus and the like. Examples of the non-virus vector include cationic liposome, membrane fusing liposome, cationic polymer and the like. The liposome is a capsule composed of phospholipid having a particle size of several 10 to several 100 nm, and a plasmid containing a CD9 gene in it can be filled in this capsule.

The expression vector containing a CD9 gene can be produced by using conventional gene engineering technologies, cell culture technologies and virus technologies (e.g., "Current Protocols in Molecular Biology, F. Ausubel et al. ed., (1994), John Wiley & Sons, Inc.", "Molecular Cloning (A Laboratory Manual), Third Edition. Volume 1-3. Josseph Sambrook & David W. Russel ed., Cold Spring Harbor Laboratory Press (Cold Spring Harbor, N.Y.) 2001", "Culture of Animal Cells; A Manual of Basic Technique, R. Freshney ed., 2nd edition (1987), Willey-Liss", "Frank K. Greham ed., Manipulation of adenovirus vectors, Chapter 11. p 109-p 128", "E. J. Murray ed., Methods in Molecular Biology, Vol. 7: Gene Transfer and Expression Protocols (1991)", "Chen, S-H, et al., Combination gene therapy for liver metastases of colon carcinoma in vivo. Proc. Natl. Acad. Sci. USA. (1995) 92, 2477-2581", and the like).

In the drug of the present invention, an expression vector containing a CD9 gene as the active ingredient and pharmaceutically acceptable auxiliaries such as excipient, carrier, solvent and the like are mixed, and the drug can be used in the form of various preparations such as injection and the like. The administration form of the drug of the present invention is not particularly restricted, and for example, injection, catheter, balloon catheter and the like can be adopted. In the case of an expression inducing substance for expressing endogenous CD9, systemic intravenous administration, or oral administration and the like can be adopted.

The amount of a CD9 gene dosed by the drug of the present invention can be appropriately controlled in view of pathological condition, age, body weight and the like of a person to be receiving dosage, and when adenovirus is used as a virus vector in a clinical test of a conventional gene therapy for a patient suffering from a heart disease, safety has been confirmed using $2 \times 10^{10}$ in terms of virus infectiosity titer pfu (plaque forming unit), therefore, this amount is a rough standard for the dosage. When liposome is used as a non-virus vector, a clinical test of a gene therapy for a person suffering from a heart disease has been conducted safely with a DNA amount of 2 mg, therefore, this amount is a rough standard for the dosage.

The drug of the present invention is used in a gene therapy, and can be applied widely for patients suffering from heart failure.

Typical pathology of heart failure include hypertrophy and dilation of heart, and hypertrophy of heart is believed to be morphological adaptation against various loads, however, it is known that, this has a limitation, and adaptation failure (compensation failure) occurs, thus, hypertrophy of a myocardial cell itself directly deteriorates the pathological condition of heart failure or other heart diseases (see, ardiology, ISHIKAWA Kyozo chief ed., 1995, Igakushoin). Therefore, further examples of heart diseases to which the drug of the present invention can be applied include ischemic heart diseases (for example, myocardial infarction), cardiomyopathy (for example, congestive cardiomyopathy, hypertrophic cardiomyopathy, restrictive cardiomyopathy), hypertensive heart diseases, valvular disease (for example, atresia of aorta valve, mitral valve and the like, or stenosis thereof), congenital heart diseases, mayocarditis and the like. Arrhythmia includes bradyarrhythmia and tachyarrhythmia, and examples of tachyarrhythmia includes superventricular arrhythmia (for example, sinus tachycardia, superventricular extrasystole, atrial fibrillation, artial flutter, superventricular tachycardia), ventricular arrhythmia (for example, ventricular extrasystole, ventricular tachycardia, ventricular fibrillation, torsade de pointes). Diseases showing generation of tachyarrhythmia as main pathological condition include WPW syndrome, long QT syndrome, Brugada syndrome, arrhythmia-inducing right ventricular dysplasia (ARVD, ARVC) (regarding arrhythmia described above, see, "Arrhythmia" (revision, Visual Text of Cardiovascular Disease 1, KASANUKI Hiroshi ed., 2000, Medical View)). The drug can be suitably used for heart diseases associated with cardiac hypertrophy or tachycardia. Heart diseases can be radically treated by inhibiting pathological hypertrophy of a myocardial cell and pathological frequent pulse of a myocardial cell (tachycardia) by expression of HB-EGF, further, pathological myocardial cell enlargement or pathological myocardial cell tachycardia (tachycardia) by expression of HGF (hepatocyte growth factor) or angiotensin 2, and normalizing the function of myocardial cells. The drug of the present invention can be used for acute heart diseases since it performs an effect in several hours after administration. In a gene therapy, a therapeutic effect for a long period of time is expected by gene expression for a long period of time, thus, the drug can be used prophylactically for preventing cardiac hypertrophy and tachycardia associated with chronic diseases such as hypertension, chronic myocardial infarction and the like.

By allowing CD9 to express in a body, heart diseases can be prevented or treated, and the prevention and treatment of heart diseases can be carried out by a gene therapy using the drug of the present invention, and also carried out by administering a substance inducing expression of endogenous CD9 and including expression of endogenous CD9 in an organism.

BEST MODES FOR CARRYING OUT THE INVENTION

Figure 1:
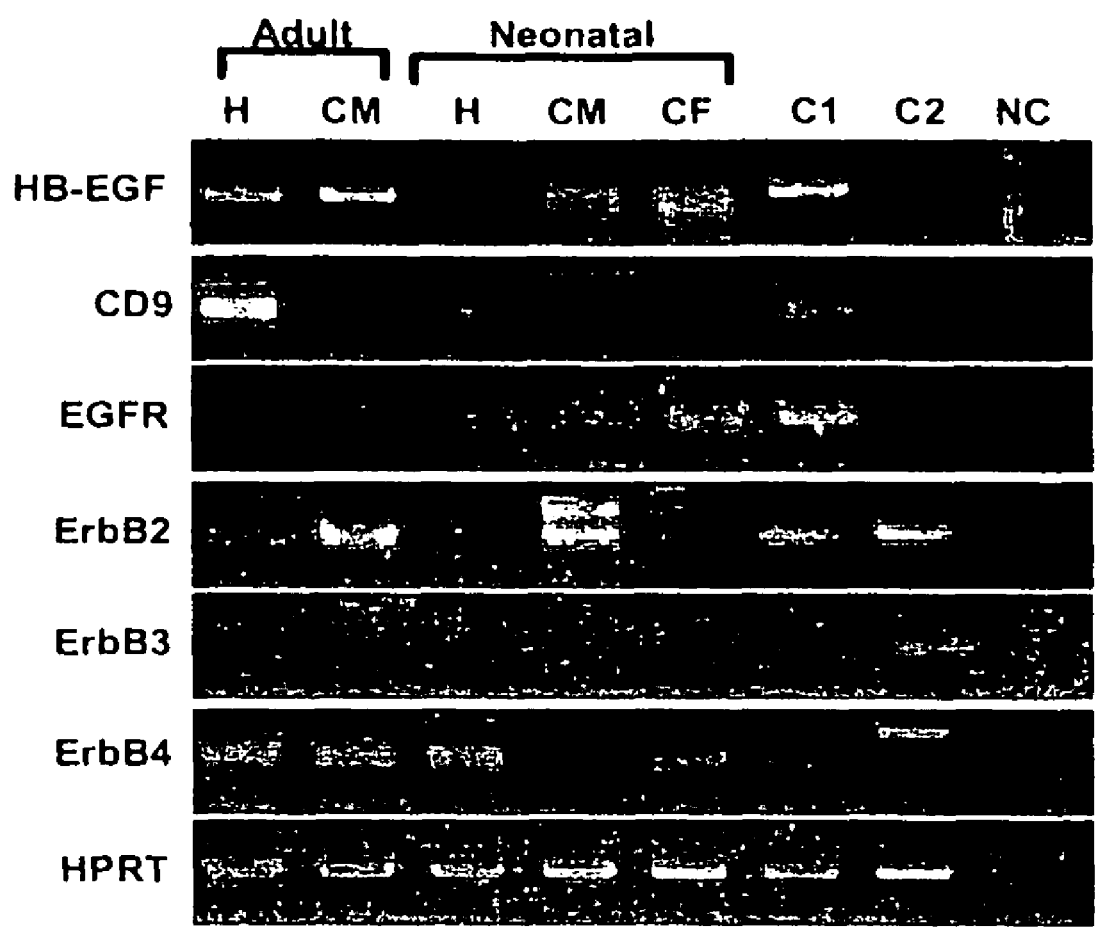
FIG. 1 shows a result of agarose electrophoresis showing expression of CD9, HB-EGF and HB-EGF receptor. H: whole heart, CM: myocardial cell, CF: cardiac fibroblast, C1; mouse lung, C2: HepG2 cell, NC: negative control, HPRT: internal control.

The present invention will be illustrated by the following examples. In the examples, gene engineering technologies and cell culturing technologies handling plasmids, DNA, various enzymes, E. coli, cultured cells and the like were carried out according to methods described in the above-mentioned "Current Protocols in Molecular Biology, F. Ausubel et al. ed., (1994), John Wiley & Sons, Inc." and "Culture of Animal Cells; A Manual of Basic Technique, R. Freshney ed., 2nd edition (1987), Willey-Liss", unless otherwise stated. Unless otherwise stated, general handling of adenovirus was carried out according to methods described in the above-mentioned "Frank L. Graham ed., Manipulation of adenovirus vectors, Chapter 11. p 109-p 128" and "E. J. Murray ed., Methods in Molecular Biology, Vol. 7: Gene Transfer and Expression Protocols (1991)", and production of adenovirus was carried out according to a method described in the above-mentioned "Chen, S-H, et al., Combination gene therapy for liver metastases of colon carcinoma in vivo. Proc. Natl. Acad. Sci. USA. (1995) 92, 2477-2581". Regarding treatment effects and phenomena, a significant difference between some groups was first analyzed by Anova assay, subsequently, an assay of an individual significant difference between each two groups was analyzed by Student t-test (asymmetrical t test between two groups). A significant difference in survival ratio was analyzed using Kaplan-Meier assay.

Adenovirus vectors used in the examples were produced as described below.

Plasmid pADL.1/RSV (B. Fang et al., Gene Therapy (1994), 1, 247-254) was a plasmid produced by incorporating, from upstream, a 0-455 base portion from 3' side of human type 5 adenovirus, Rous sarcoma virus long-term repeat (RSV) promoter, multi cloning site, poly A signal sequence of Bovine growth hormone, and a 3328-5788 base portion from 3' side of human type V adenovirus, into pBR322 plasmid, and offered from Shu-Hsia Chen (Mount Sinai University). pADL.1/RSV plasmid was digested with restriction enzymes Hind III and Not I and purified, to give a vector to be used for ligation. On the other hand, plasmids pRcHBEGF and pRcCD9, containing cDNA of the whole length of open reading frame of human HB-EGF and cDNA of the whole length of open reading frame of monkey CD9, respectively, in plasmid pRc/CMV (Invitrogen), were offered from Mekata Eisuke (Osaka University). From both the plasmids pRcHBEGF and pRcCD9, the whole lengths of HB-EGF cDNA and CD9 cDNA were excised, respectively, using restriction enzymes Hind III and Not I, and these were subjected to agarose gel electrophoresis, the intended DNA fragment was excised and purified to give an insert to be used for ligation. Thus treated pADL.1/RSV vector and HB-EGF cDNA, CD9 cDNA inserts were subjected to a ligation reaction with T4 DNA ligase, to obtain pADL.1/RSV-HB-EGF, and pADL.1/RSV-CD9. Further, pADL.1/RSV-HB-EGF and pADL.1/RSV-CD9 were, together with pJM17 (Microbix Biosystems Inc.) of a plasmid containing a gene other than E1 region of human type V adenovirus, co-infected in 293 cells by a calcium phosphate method. By this, a plaque containing correct intended adenovirus produced by homologous recombination emerged 10 to 14 days after co-infection. This plaque was picked up, and correct non-proliferation type recombinant adenoviruses Ad.HB-EGF and Ad.CD9 expressing intended HB-EGF and CD9 were confirmed by immune staining using an anti-HB-EGF antibody (M-18:sc-1414, SANTA CRUZ) and an anti-CD9 antibody (ALB6, IMMUNOTECH), and the like, then, viruses were proliferated by 293 cells, and concentrated and purified by a gradient centrifugal method for cesium chloride.

A recombinant adenovirus Ad.LacZ expressing a LacZ gene of E. coli used for gene transferring was produced in the same method as descriebd above, and details of the Ad.LacZ production method are described in Proc. Natl. Acad. Sci. U.S.A. (1995) 92, 2577-2581. Ad.dE1.3 contains no incorporated CD9 and HB-EGF, thus, this is a control recombinant adenovirus not expressing these genes at all. pADL.1/RSV and pJM17 containing no incorporated CD9 and HB-EGF were co-infected in 293 cells as described above, and subjected to the same method and process to produce Ad.dE1.3. HB-EGF is described in Higashiyama, S., et al. Science 251, 936-939 (1991), and its accession No. of Gene Bank is N60278. As CD9, monkey CD9 was used, and the monkey CD9 is reported as DRAP27 (diphtheria toxin receptor-associated protein) (Mitamura T, et al: J cell Biol., 118(6): 1389-1399, 1992, Gene Bank accession No. is BAA01569), and the gene sequence thereof is believed to be almost the same and its function is also believed to be the same as human CD9. Evaluation of cell area of a myocardial cell and evaluation of beat number of a myocardial cell conducted in the following experiment system are based on a fact that cardiac hypertrophy is defined as hypertrophy of a myocardial cell and tachycardia is defined as increase in beat number of a myocardial cell (see, worldwide most famous and authoritative text "Braunwald's HEART DISEASE A textbook of cardiovascular medicine, 6$^{th}$ edition, 2001").

EXAMPLE 1

EXPRESSION OF CD9 AND THE LIKE IN WHOLE HEART AND MYOCARDIAL CELL OF RAT AND MOUSE

Each endogenous expression of CD9, HB-EGF or a group of receptors of HB-EGF (EGFR, ErbB2, ErbB3, ErbB4) in the whole heart and myocardial cells was checked using a RT-PCR method. Myocardial cells and whole heart from 8-week old adult SD rats and 1-day old neonatal BALB/C mice were enzymatically treated with collagenase type 2 (WOR: CLS 2, Funakoshi catalogue No. 45004177), and isolated. Then, 1 ml of sepazole RNA I Super (NACALAI TESQUE catalogue No. 304-86) was added to homogenize, and the homogenized mixture was separated into an aqueous phase and a phenol phase by chloroform, and the aqueous phase was precipitated with isopropanol. After centrifugal separation, the product was suspended with 70% ethanol, and further centrifugally separated, to extract RNA. 1 μg of total RNA was reverse-transcribed with Super Script II reverse transcriptase (Invitrogen), and cDNA was amplified by a PCR method.

A sense primer (5'-CCGTGATGCTGAAGCTCTTT-3', SEQ ID No. 1) and an anti-sense primer (5'-CCAAGACTG-TAGTGTGGTCAT-3', SEQ ID No. 2) (Yoshizumi M., et al. : J. Biol. Chem., 267, 9467-9469, 1992) of HB-EGF, and a sense primer (5'-AGCAAGTGCATCAAATACC-3', SEQ ID No. 3) and an anti-sense primer (5'-AATCACCTCATCCT-TGTGG-3', SEQ ID No. 4) of CD9 were synthesized by requested Hokkaido System Science Co., Ltd. A group of receptors of HB-EGF referred to Sundaresan S, et al: Endocrinology 139: 4756-4764, 1988, and a sense primer (5'-ACAACTGTGAAGTGGTCCT-3', SEQ ID No. 5) and an anti-sense primer (5'-TTCCTGTAAGTTCCGCAT-3', SEQ ID No. 6) of EGFR, a sense primer (5'-AGCTGGTGACA-CAGCTTA-3', SEQ ID No. 7) and an anti-sense primer (5'-TGGTTGGGACTCTTGAC-3', SEQ ID No. 8) of ErbB2, a sense primer (5'-GACCTAGACCTAGACTT-3', SEQ ID No. 9) and an anti-sense primer (5'-TCTGATGACTCTGATGC-3', SEQ ID No. 10) of ErbB3, and a sense primer (5'-CATC-TACACATCCAGAACA-3', SEQ ID No. 11) and an anti-sense primer (5'-AAACATCTCAGCCGTTGCA-3', SEQ ID No. 12) of ErbB4 were synthesized by requested Hokkaido System Science Co., Ltd. As an internal control, hypoxanthine phosphoribosyltransferase (HPRT) was used.

As a positive control, HepG2 cells of lung of the above-mentioned neonatal mouse and human liver cancer cells (offered by Medical Cellular Resource Center, Institute of Development, Aging and Cancer, Tohoku University) were used. In a PCR method for HB-EGF and CD9, using Promega Taq (Promega catalogue No. M1865), a cycle of heat denaturing at 94° C. for 30 seconds, annealing at 56° C. for 1 minute and elongation reaction at 72° C. for 1 minute was repeated 38 times, and in a PCR method for a group of receptors of HB-EGF and HPRT, TAKARA Ex Taq (TAKARA catalogue No. RR001A) were used, and the analogous procedure was performed at an annealing temperature of 55° C. As PCR thermal cycler, TAKARA TP-400 was used.

As shown in FIG. 1, expression of HB-EGF was observed in heart both in adult rats and neonatal mice, and particularly, expression was stronger in a cultured myocardial cell, thus, it is recognized that HB-EGF was highly expressed in a myocardial cell itself in heart. Though it is recognized that ErbB2 and ErbB4 were expressed strongly in a cultured myocardial cell both in adult rats and neonatal mice, expression of EGFR was not clear in adult rats and strong expression thereof was recognized in neonatal mice. Expression of ErbB3 was not recognized in both adult rats and neonatal mice. On the other hand, though expression of CD9 was recognized in the whole heart of adult rats, expression thereof was not clear in its cultured myocardial cell, and expression thereof was not recognized both in the whole heart and cultured myocardial cells of neonatal mice. Thus, it was clarified that ErbB2 and ErbB4 included in a group of receptors of HB-EGF are relatively highly expressed in myocardial cells, while CD9 is scarcely expressed in myocardial cells.

EXAMPLE 2

CONFIRMATION OF GENE TRANSFER EFFICIENCY OF ADENOVIRUS VECTOR

Figure 2:
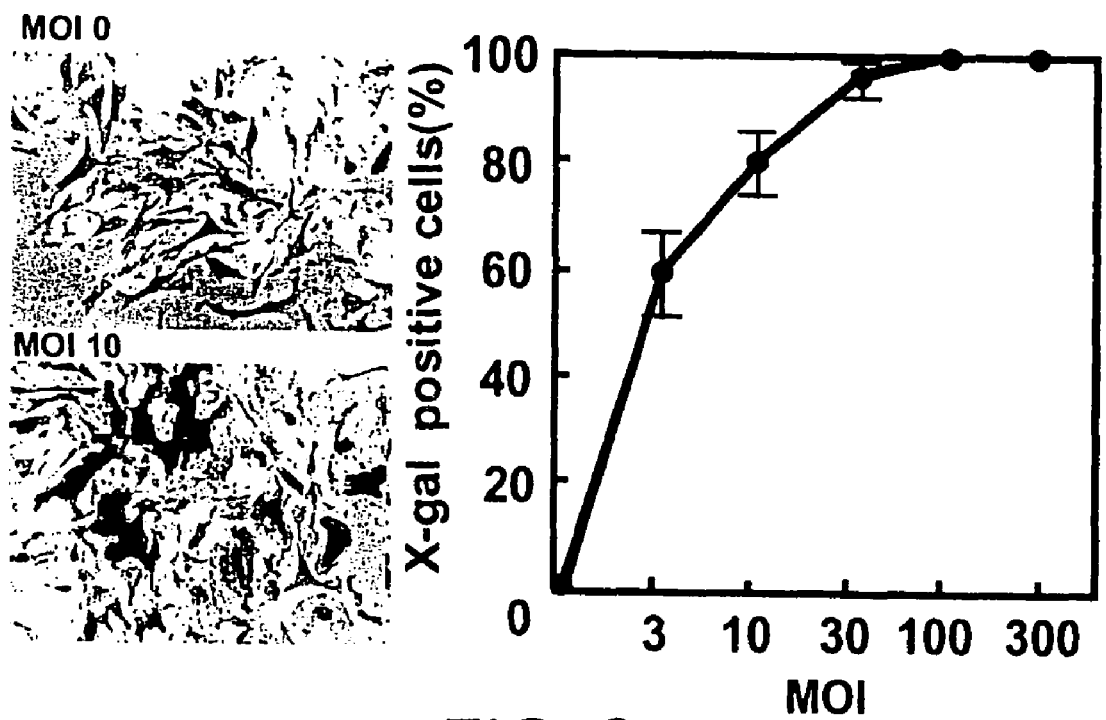
FIG. 2 shows a graph showing a gene transferring efficiency of Ad. LacZ to a myocardial cell of a neonatal mouse, and a micrograph of a cultured myocardial cell stained with X-gal.

Myocardial cells (Aoyama T, et al: Cardiovasc Res., 55: 787-798, 2002) isolated from a 1-day old neonatal BALB/C mouse by collagenase type 2 (WOR: CLS 2, Funakoshi catalogue No. 45004177) were disseminated on a 4-well chamber slide (Nunc: Lab-Tek, Permanox, catalogue No. 15 77437) coated with mouse laminin (Biomedical Technologies Inc. catalogue No. BT-276) at a concentration of $5\times 50^5/500$ μl/well, and maintained by a low glucose DMEM medium (SIGMA catalogue No. D6046) containing penicillin (100 units/ml) and streptomycin (100 μg/ml), 5% inactivated Australian fetal bovine serum, and cultured in a humidified culture vessel under 95% air −5% carbon dioxide at 37° C. Gene transferring efficiency of an adenovirus vector into the resultant primary culture myocardial cell, and expression thereof were confirmed. That is, primary culture myocardial cells were infected with Ad. LacZ at MOI (multiplicity of infection: 1 MOI=1 plaque forming unit/cell) diluted to 300, 100, 30, 10, 3 and 0, and 48 hours after, X-gal staining was effected. As shown in FIG. 2, an excellent gene transferring efficiency of 96% at MOI 30, and 80% or more at MOI 10 were obtained. Based on this result, adenovirus was infected at MOI 10 to 30, in the following experiment, and expressed sufficiently for 24 hours, then, the medium was exchanged, further, washed with serum-free medium liquid and used. When HB-EGF, angiotensin 2 or HGF is allowed act, culturing in serum-free culture liquid was carried out for further 24 hours.

EXAMPLE 3

IMMUNOHISTOCHEMICAL STAINING OF MYOCARDIAL CELL

The cultured myocardial cells of neonatal mice obtained above were fixed with 4% paraformaldehyde for 10 minutes, a cell membrane was perforated with 0.05% TritonX100, and blocked with 10% skimmed milk (Snow Brand Milk Products Co., Ltd.) for 60 minutes. Thereafter, a primary antibody (mouse monoclonal antibody CD9 (clone ALB6), IMMUNOTECH catalogue No. 0117) diluted 50-fold (2 μg/ml) and a goat polyclonal antibody HB-EGF (M-18) (SANTA CRUZ catalogue No. sc-144) diluted 100-fold were reacted for 1 hour, and visualization of HB-EGF was carried out while labeling with anti-goat Alexa 568 (MOLECULAR PROBES catalogue No. A-11057) and visualization of CD9 was carried out while labeling with anti-mouse Alexa 488 (MOLECULAR PROBES catalogue No. A-11029). Nucleus staining was carried out for 5 minutes with Hoechst 33342 (MOLECULAR PROBES catalogue No. H-3570) diluted 1000-fold. F-actin was labeled with rhodamine phalloidin (MOLECULAR PROBES catalogue No. R-415) diluted 500-fold and recognized. Recording of an observed image was performed by a cofocal laser microscope (Carl Zeiss product No. LSM 510). Sufficient transferring efficiency at MOI 10 was confirmed, then, expression and localization after gene transferring into a myocardial cell by Ad.HB-EGF, Ad.CD9, and Ad.HB-EGF+Ad.CD9 were confirmed by fluorescent immunohistostaining. The results are shown in Table 3.

Figure 3:
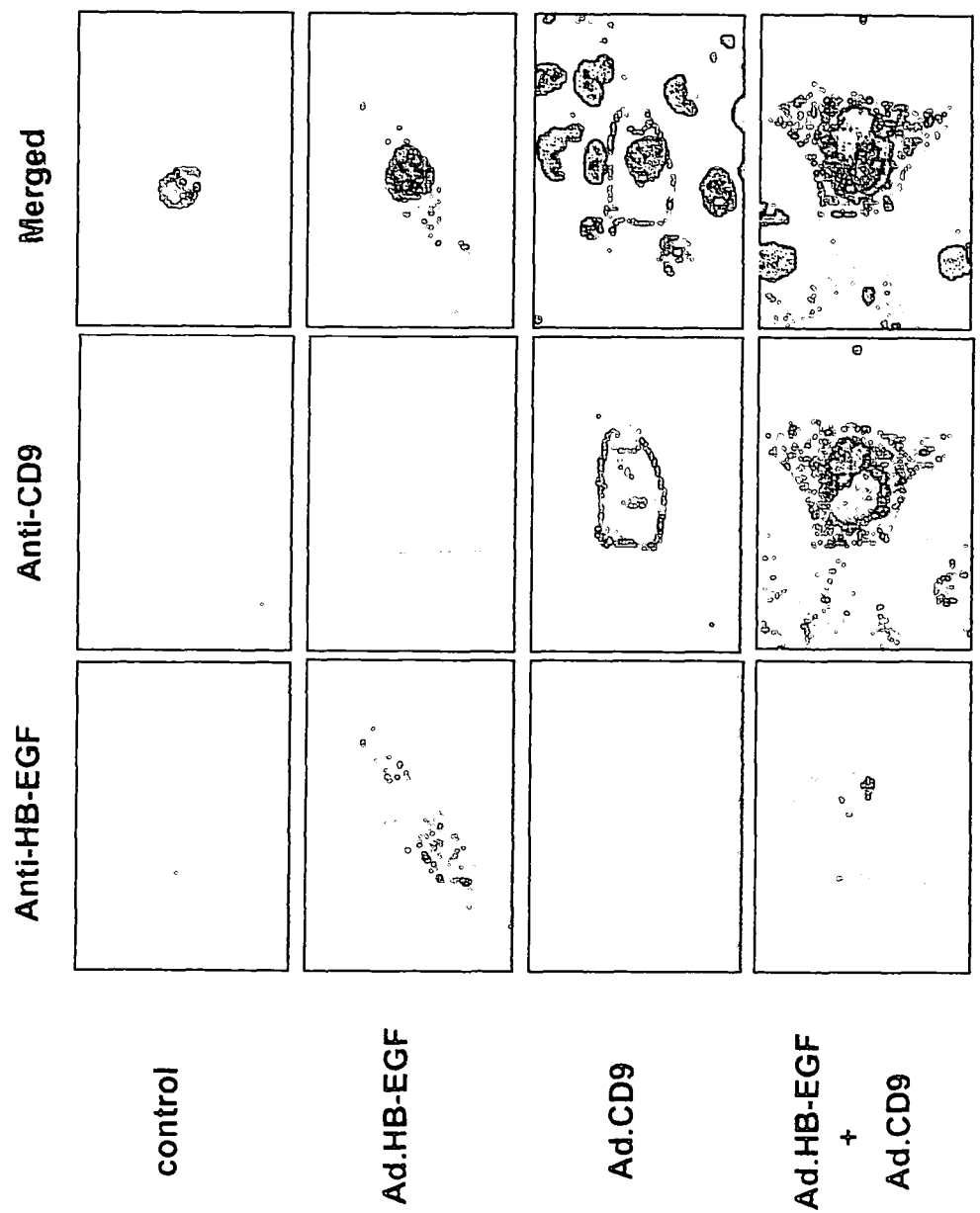
FIG. 3 shows micrographs of myocardial cells obtained by each gene-transferring Ad. HB-EGF, Ad. CD9 or Ad. HB-EGF+Ad. CD9 to myocardial cells of a neonatal mouse and effecting immunohistochemical staining on these cells.

As shown in FIG. 3, an expression pattern when only HB-EGF was singly gene-transferred was stained in the form of grain in a cell, and when only CD9 was singly gene-transferred, the surface of cell membrane was stained. However, when HB-EGF and CD9 were co-expressed, change of localization patterns of the proteins was confirmed. That is, when CD9 is singly gene-transferred, an expression protein of the transferred CD9 gene localizes on a membrane which is an original expression site of endogenous CD9, however, when HB-EGF and CD9 were strongly expressed together, it was found that a CD9 protein moves into a cell together with a HB-EGF protein.

EXAMPLE 4

CELL AREA AND BEAT NUMBER OF MYOCARDIAL CELL

On the myocardial primary culture cell of a neonatal mouse obtained above, CD9, HB-EGF or CD9+HB-EGF (each at MOI 10) is strongly expressed each using Ad.CD9, Ad.HB-EGF, or Ad.CD9+Ad.HB-EGF, and change of a myocardial cell after 24 hours was investigated morphologically and physiologically. A myocardial cell was fixed with 4% paraformaldehyde for 10 minutes, the cell area was measured using PIXEL count (Adobe Photoshop).

Figure 4:
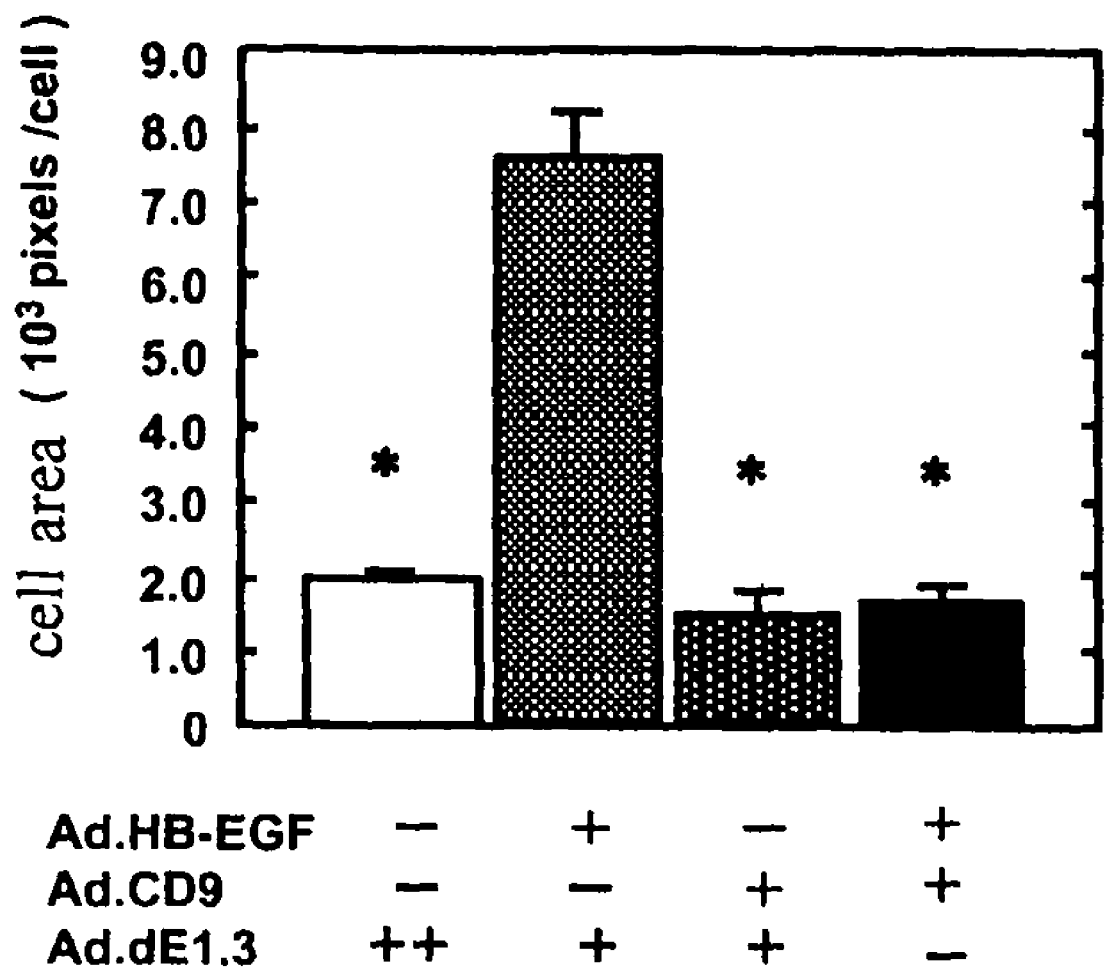
FIG. 4 shows a graph showing areas of myocardial cells after each gene-transferring Ad. HB-EGF, Ad. CD9 or Ad. HB-EGF+Ad. CD9 to myocardial cells of a neonatal mouse.

As shown in FIG. 4, the cell area of the myocardial cell containing gene-transferred HB-EGF showed a significant increase (*p<0.05 vs Control) based on the control (HB-EGF and CD9 genes were not transferred), and the cell area of the myocardial cell containing single gene-transferred CD9 showed no significant change. On the other hand, the cell area of the myocardial cell of CD9 +HB-EGF genes transferred group significantly suppressed increase by HB-EGF.

Figure 5:
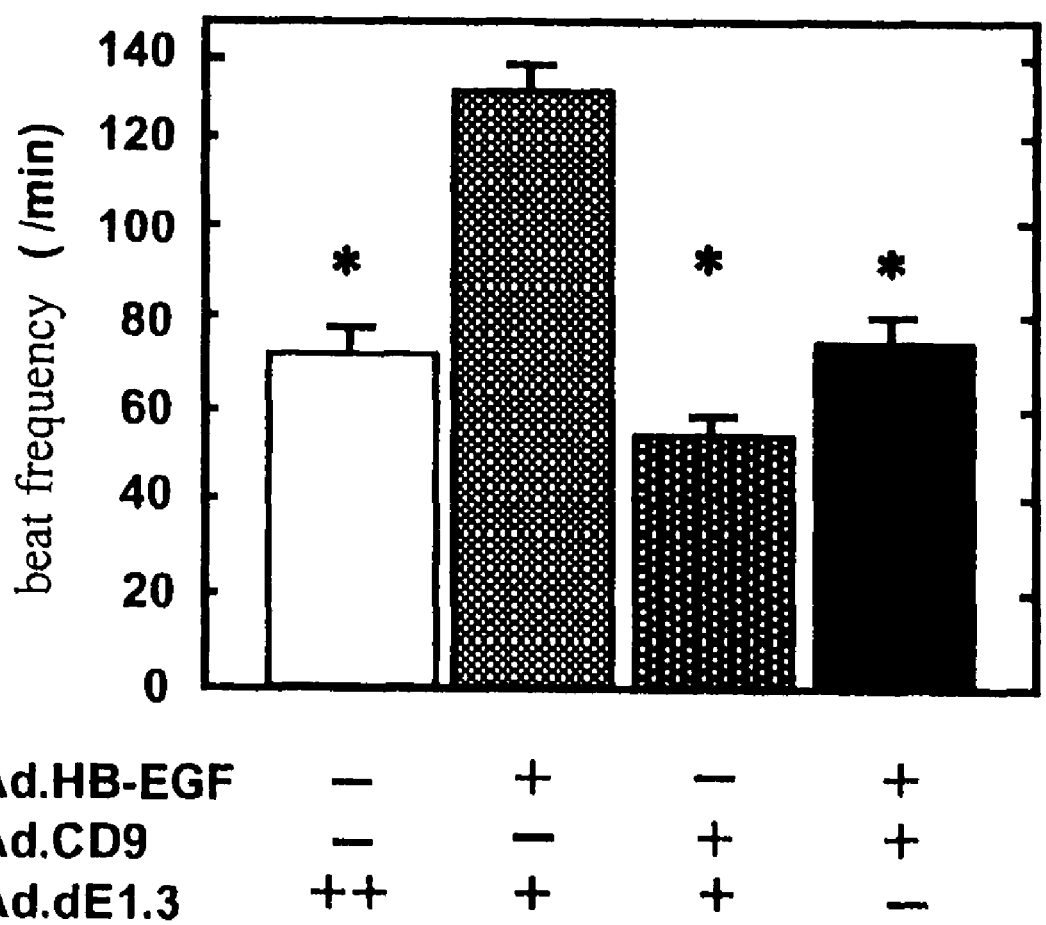
FIG. 5 shows a graph showing beat number of myocardial cells after each gene-transferring Ad. HB-EGF, Ad. CD9 or Ad. HB-EGF+Ad. CD9 to myocardial cells of a neonatal mouse.

Next, the beat of myocardial cells each containing gene-transferred CD9, HB-EGF, or CD9+HB-EGF described above was recorded using a video microscope observation system (OLYMPUS microscope IX 70+CCD camera CS 900). As a result, as shown in FIG. 5, the beat number of a myocardial cell containing gene-transferred HB-EGF showed a significant increase (130±10/min. against control 70±8/min.), however, the beat number of a myocardial cell containing gene-transferred CD9+HB-EGF was approximately the same (76±10/min.) as the control, indicating inhibition of the action of HB-EGF by CD9 (*p<0.05 vs control).

A myocardial primary culture cell of a neonatal mouse was infected with Ad.CD9 at MOI 30 to cause gene transferring, CD9 was strongly expressed, and 24 hours later, human recombinant HB-EGF (rHB-EGF, R&D system, catalogue No. 259-HE) (concentration 10 ng/ml), angiotensin 2 (SIGMA, catalogue No. A-9525) (concentration 100 nM) and human recombinant HGF (rHGF, R&D system, catalogue No. 294-HG) (concentration 10 ng/ml), respectively were added into the culture solution, and allowed to act on myocardial cells for 24 hours. Thereafter, the myocardial cells were fixed with 4% paraformaldehyde, the presence or absence of transferring of CD9 was confirmed by immunostaining, and the extent of formation of muscle fiber was checked by F-actin staining. The myocardial cell (see, photograph of Anti-CD9) containing gene-transferred CD9 shown in FIG. 6 suppressed the hypertrophy action of a myocardial cell by human recombinant HB-EGF, angiotensin 2 and human recombinant HGF, as is understood from photograph images mergeing a CD9 immunostained image and a F-actin stained image.

Regarding myocardial cells obtained by allowing CD9 to strongly express and each adding human recombinant HB-EGF, angiotensin 2 or human recombinant HGF to the culture solution, the area ratio of the myocardial cell in each group to the area of a myocardial cell of control containing no gene-transferred CD9 was analyzed, the area of control being 1. Regarding change in beat number of a myocardial cell, Ad.CD9 or Ad.dE1.3 (control) was allowed to act sufficiently at MOI 30, from 24 hours before each addition of human recombinant HB-EGF, angiotensin 2, or human recombinant HGF. After confirmation of the presence of a beating cell, the product was washed three times with a serum-free culture solution, human recombinant HB-EGF, angiotensin 2 and human recombinant HGF, respectively were added in the same amount as in quantification of hypertrophy of a myocardial cell, and 3 hours later, 20 or more myocardial cells were observed each for 5 minutes or more using a cultured cell video observation system (OLYMPUS microscope product NO. IX 70 and CCD camera product No. CS 900), and the beat number in 1 minute was measured.

Figure 6:
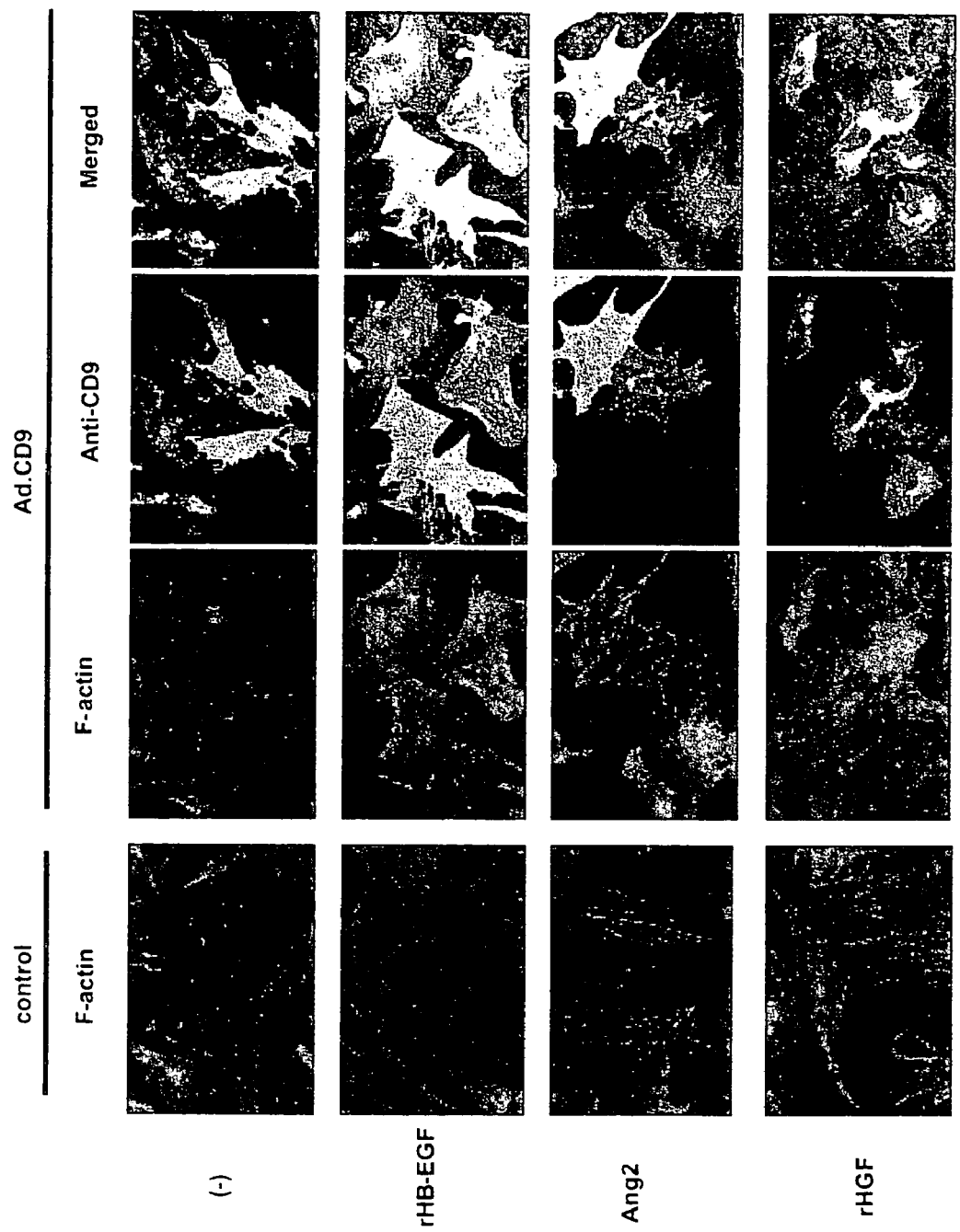
FIG. 6 shows micrographs of myocardial cells when human recombinant HB-EGF (rHB), angiotensin 2 (Ang2) or human recombinant HGF (rHGF) is allowed to act on myocardial cells of a neonatal mouse expressed by gene-transferring Ad. CD9.
Figure 7:
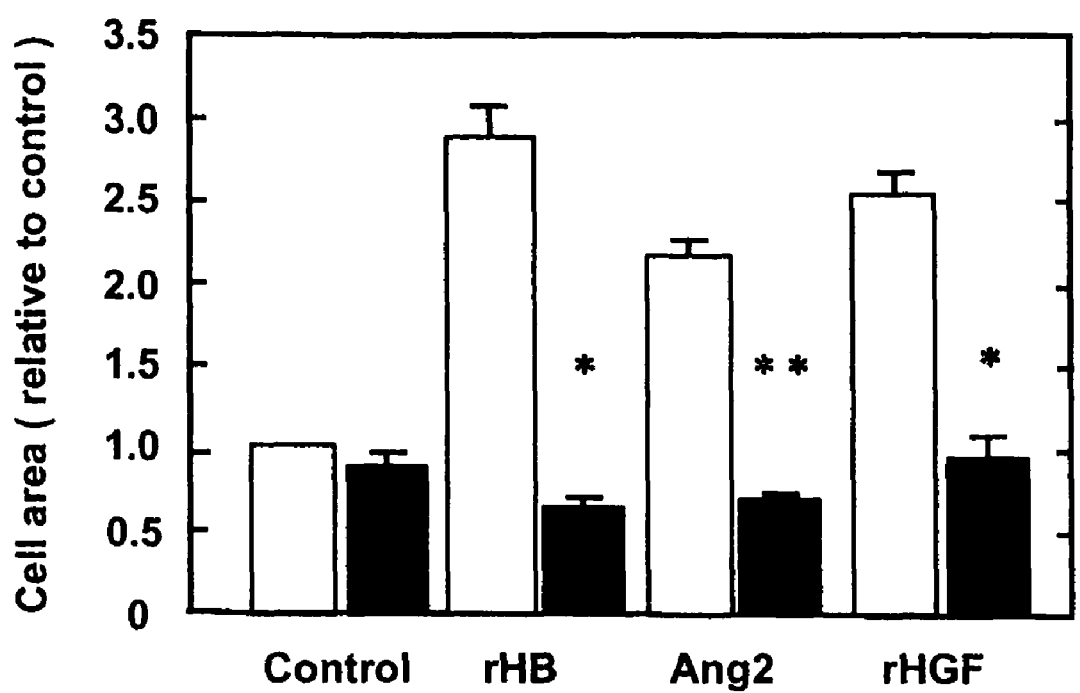
FIG. 7 shows a graph showing cell areas of myocardial cells when human recombinant HB-EGF (rHB), angiotensin 2 (Ang2) or human recombinant HGF (rHGF) is allowed to act on myocardial cells of a neonatal mouse expressed by gene-transferring Ad. CD9. In the graph, solid means gene-transferring of CD9.
Figure 8:
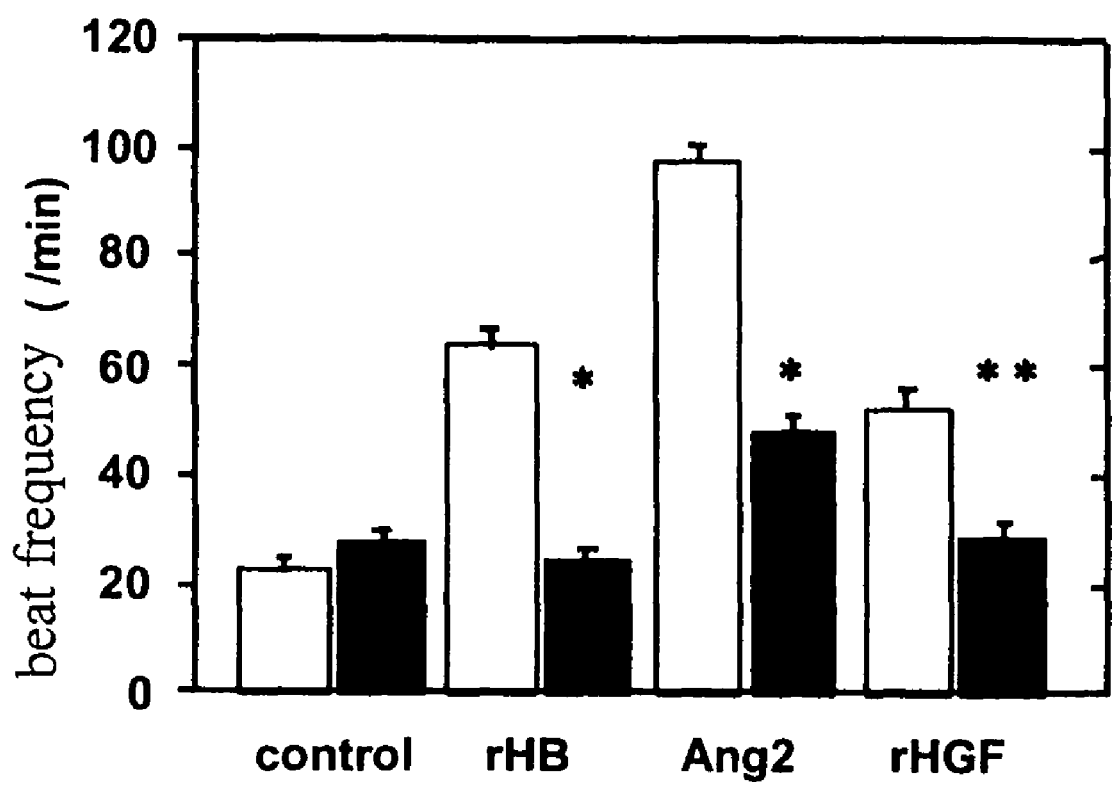
FIG. 8 shows a graph showing beat number of myocardial cells when human recombinant HB-EGF (rHB), angiotensin 2 (Ang2) or human recombinant HGF (rHGF) is allowed to act on myocardial cells of a neonatal mouse expressed by gene-transferring Ad. CD9. In the graph, solid means gene-transferring of CD9.

As shown in FIG. 6, when any one of human recombinant HB-EGF, angiotensin 2 and human recombinant HGF was added, formation of muscle fiber and hypertrophy of a myocardial cell could be confirmed in all cases, however, in a myocardial cell in which CD9 had been previously strongly expressed and its expression had been confirmed, hypertrophy of a myocardial cell and formation of muscle fiber were suppressed. The cell area was statistically significant as shown in FIG. 7. For example, human recombinant HB-EGF alone: 2.8±0.5-fold to control and CD9+ human recombinant HB-EGF: 0.7±0.1-fold to control, and also in the case of angiotensin 2 and rHGF, CD9 suppressed hypertrophy of a myocardial cell likewise (*p<0.05 vs Control, **p<0.001 vs Control). The beat number of a myocardial cell showed significant increase by the action of human recombinant HB-EGF, angiotensin 2 and human recombinant HGF as shown in FIG. 8, and it was confirmed that this action is canceled by CD9 (*p<0.05 vs Control, **p<0.001 vs Control). By this, it has become apparent that CD9 suppresses a hypertrophy action of a myocardial cell and a heart positive inotropic action also in vitro.

EXAMPLE 5

INHIBITION OF PHOSPHORYLATION IN SIGNAL TRANSMISSION

Figure 9:
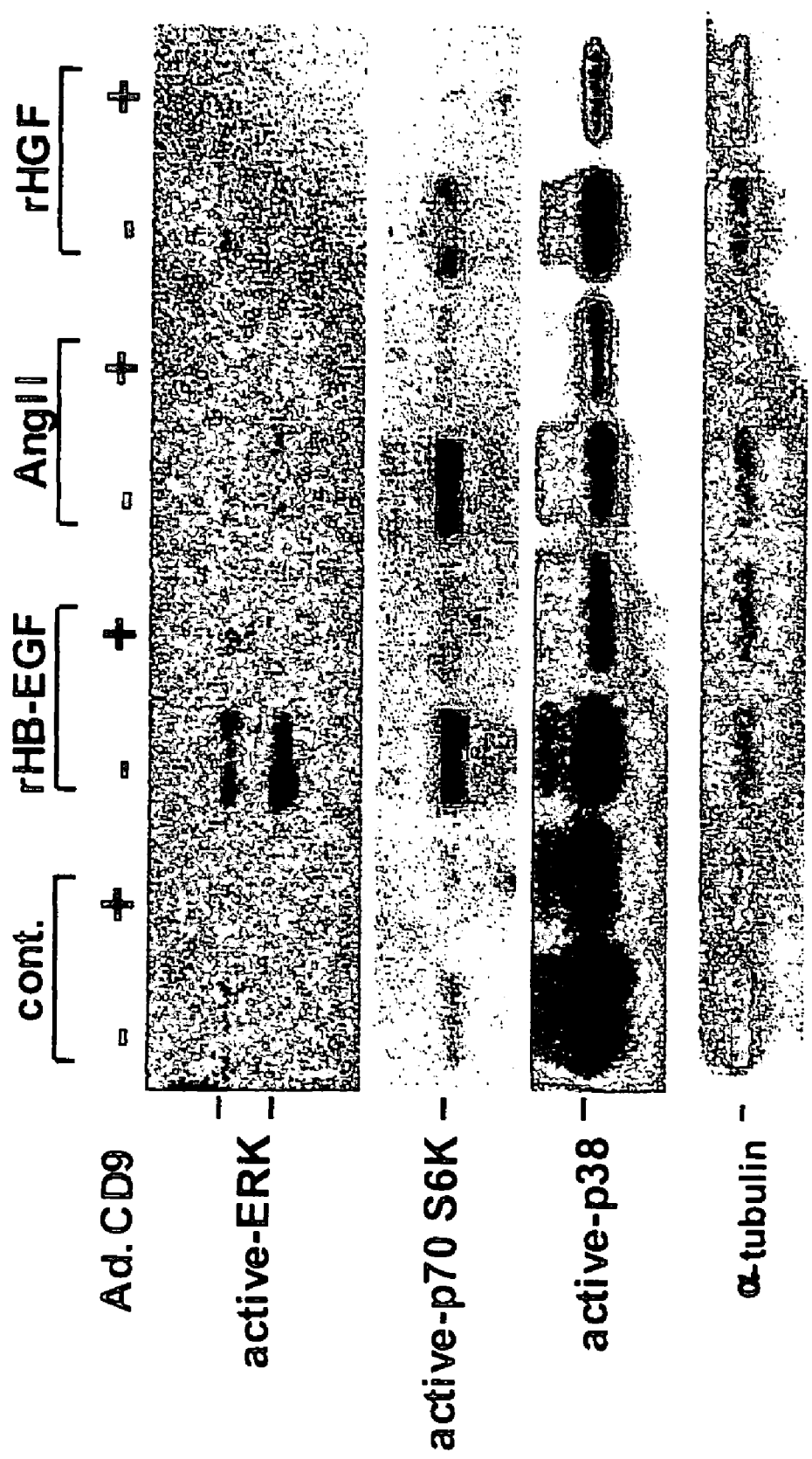
FIG. 9 shows photograph images showing analysis by Western blotting of the extent of phosphorylation in signal transmission depending on the presence or absence of expression of CD9.

Next, for investigating the mechanism of CD9, phosphorylation of MAPK (MAP kinase) of intracellular information transmission was carried out. From myocardial cells of which observation of beat had been completed, a protein was extracted by a Bradford method using a protein assay kit (Biorad, catalogue No. 500-0002JA), and allowed to migrate each in an amount of 3 μg on SDS-PAGE, and recognized by Western Blotting. As a result, as shown in FIG. 9, phosphorylation of active-ERK, active-p70 S6K and active-p38 was suppressed (active-p38 was suppressed slightly) by the action of CD9 by using pERK(E-4) (SANTACRUZ catalogue No. sc-7383), p-p70 S6K(A-6) (SANTACRUZ catalogue No. sc-8416) and p-p38(D-8) (SANTACRUZ catalogue No. sc-7973), and it was guessed that signal transmission was inhibited. Inhibition of signal transmission was observed not only by the action of human recombinant HB-EGF but also by the action of angiotensin 2 and human recombinant HGF likewise, suggesting correlation to a signal transmission route of HB-EGF, angiotensin 2 and HGF.

Color development was labeled with a secondary antibody of HRP, and light was emitted by super signal West Pico chemical fluorescent color developing substance (PIERCE catalogue No. 34077). As a protein of internal control, α-tublin (DM1A) (SIGMA catalogue No. T-9026) was detected by Western blotting likewise.

EXAMPLE 6

IMPROVEMENT OF CARDIAC FUNCTION IN MYOCARDIAL INFARCTION ANIMAL MODEL 8 to 12-week adult male mice C57/BL6 were subjected to tracheotomy, anesthetized generally (GOH nitrous oxide/oxygen/halothane) by an anesthesia machine (Kimura Medical Instrument Co., Ltd. product No. compact-15), then, subjected to thoracotomy. A coronary artery was ligated permanently with 2-0 nylon thread, to produce myocardial infarction animal models. A PBS solution containing each $1 \times 10^{11}$ particles of Ad.HB-EGF, Ad.dE1.3 and Ad.HB-EGF+ Ad.CD9 dissolved in 100 ul of PBS was directly sprayed on the epicardium side of a cardiac muscle, and thoracotomy was performed. 4 days later, serum was collected, and 1 week later (1 week model after myocardial infarction) and 8 weeks later, models were tenderly sacrificed and evaluated. In the myocardial infarction 1 week model, left ventricular ejection fraction (LVEF), left ventricular diastolic diameter (LVDd), left ventricular systolic diameter (LVSd), left ventricular septum thickness (LVSt) and posterior wall thickness (PWt) were measured by echocardiography (AROKA, probe: 7.5 MHz product No. SSD-2000) From right carotid artery, an artery pressure monitor column (Millar Instruments catalogue No. SPR 407) was invasively inserted into aorta and left ventricle, and left ventricular systolic pressure (LVSP), left ventricular end diastolic pressure (LVEDP), left ventricular maximum positivity dP/dt and left ventricular maximum negativity dP/dt were measured (PowerLab system ver 4.2 ADInstruments). After blood collection, internal organs (heart, lung, liver, kidney, spleen) were collected.

Figure 10:
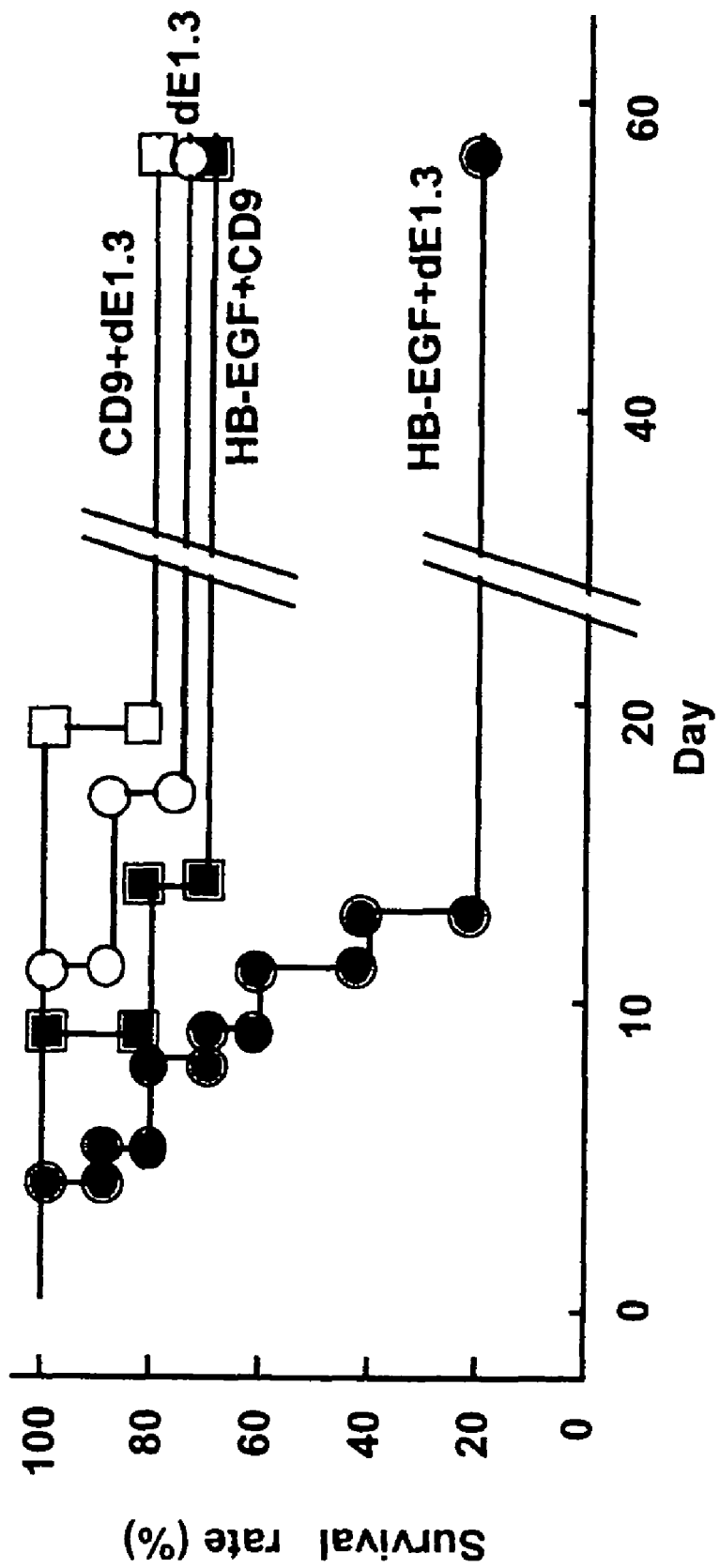
FIG. 10 shows a survival curve in a chronic heart failure model of adult mice 8-week after myocardial infarction.

FIG. 10 shows a survival curve until 8 weeks in the chronic phase. Mice (HB-EGF+del.3) containing only gene-transferred HB-EGF died in the acute phase (within approximately 2 weeks), when CD9 was gene-transferred simultaneously, mice (HB-EGF+CD9) could survive (p<0.05).

Figure 11:
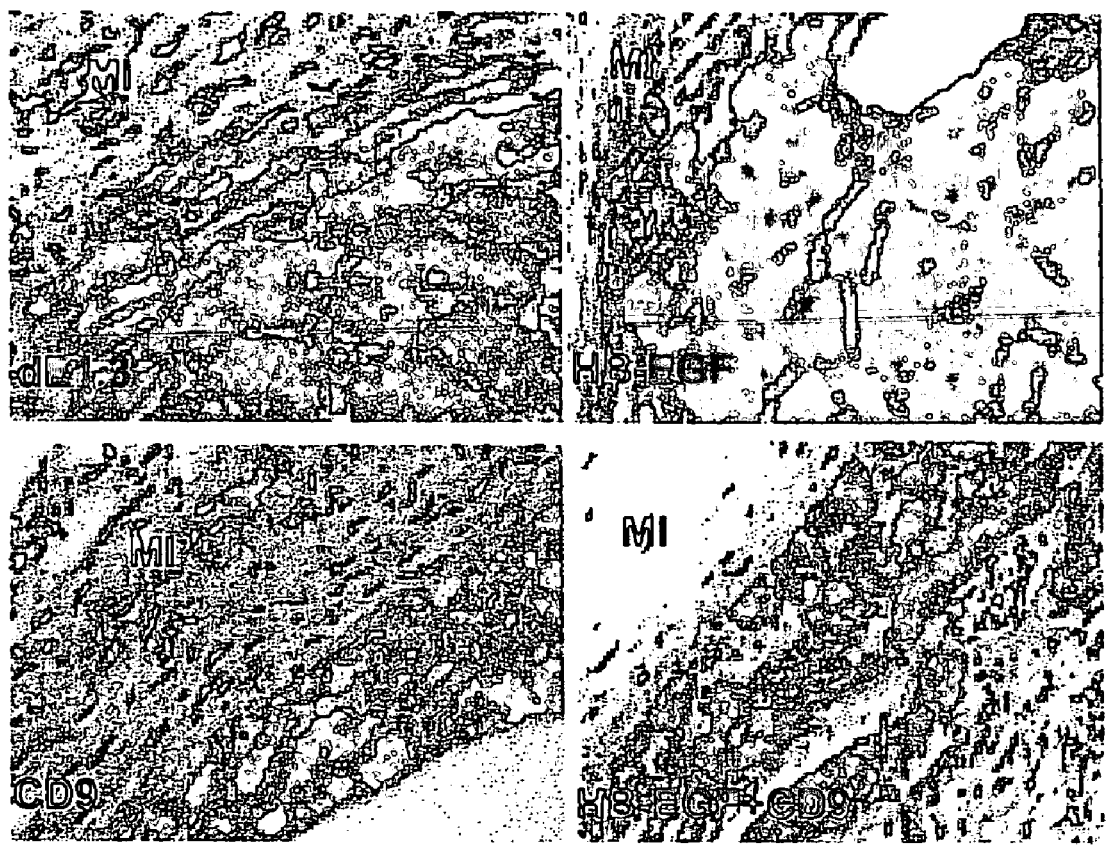
FIG. 11 shows micrographs of border zones of myocardial cells in a chronic heart failure model of adult mice 8-week after myocardial infarction.
Figure 12:
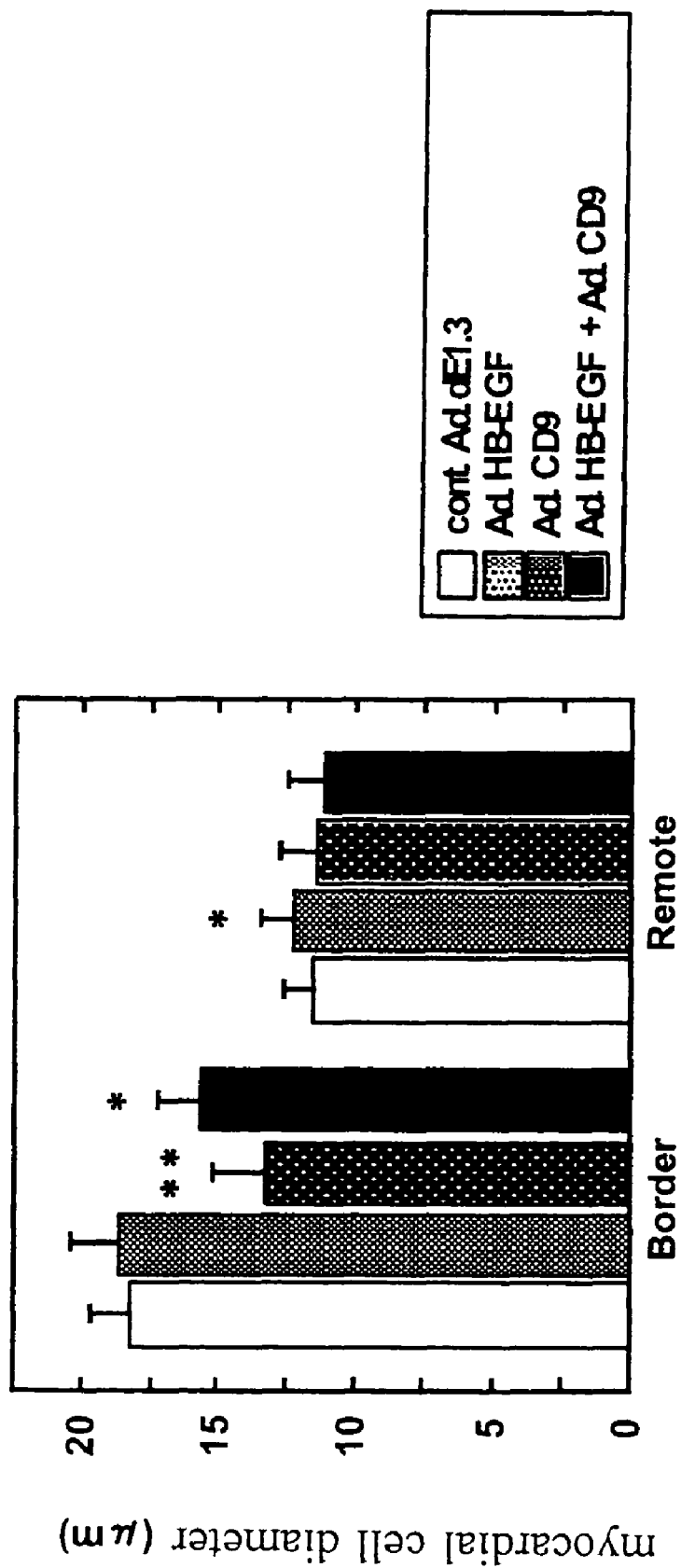
FIG. 12 shows a graph showing the diameter of a myocardial cell in border zone and remote zone in a chronic heart failure model of adult mice 8-week after myocardial infarction.

Next, a histological investigation was carried out. Heart of a mouse in chronic phase 8 weeks was sliced, and fixed with 10% formalin. After paraffin embedding, the sample was cut, then, stained with HE. As shown in FIG. 11, mice containing simultaneously gene-transferred CD9 showed suppression of compensatory hypertrophy of heart as compared with mice containing gene-transferred HB-EGF. Using each section, cardiac muscle cell diameter was measured in border zone (Border: boundary region between a myocardial infarction part and a normal part) and remote zone (Remote: normal cardiac muscle part remote from a myocardial infarction part) (20 or more each samples for each zone) using LUZEX F system (manufactured by NIRECO). As shown in FIG. 12, compensatory hypertrophy of heart was observed also in the HB-EGF group in the border zone, which was also observed in the control group, and by simultaneous gene-transferring of CD9, its hypertrophy action of heart was suppressed (*p<0.05 vs control, **p<0.001 vs control).

Figure 13:
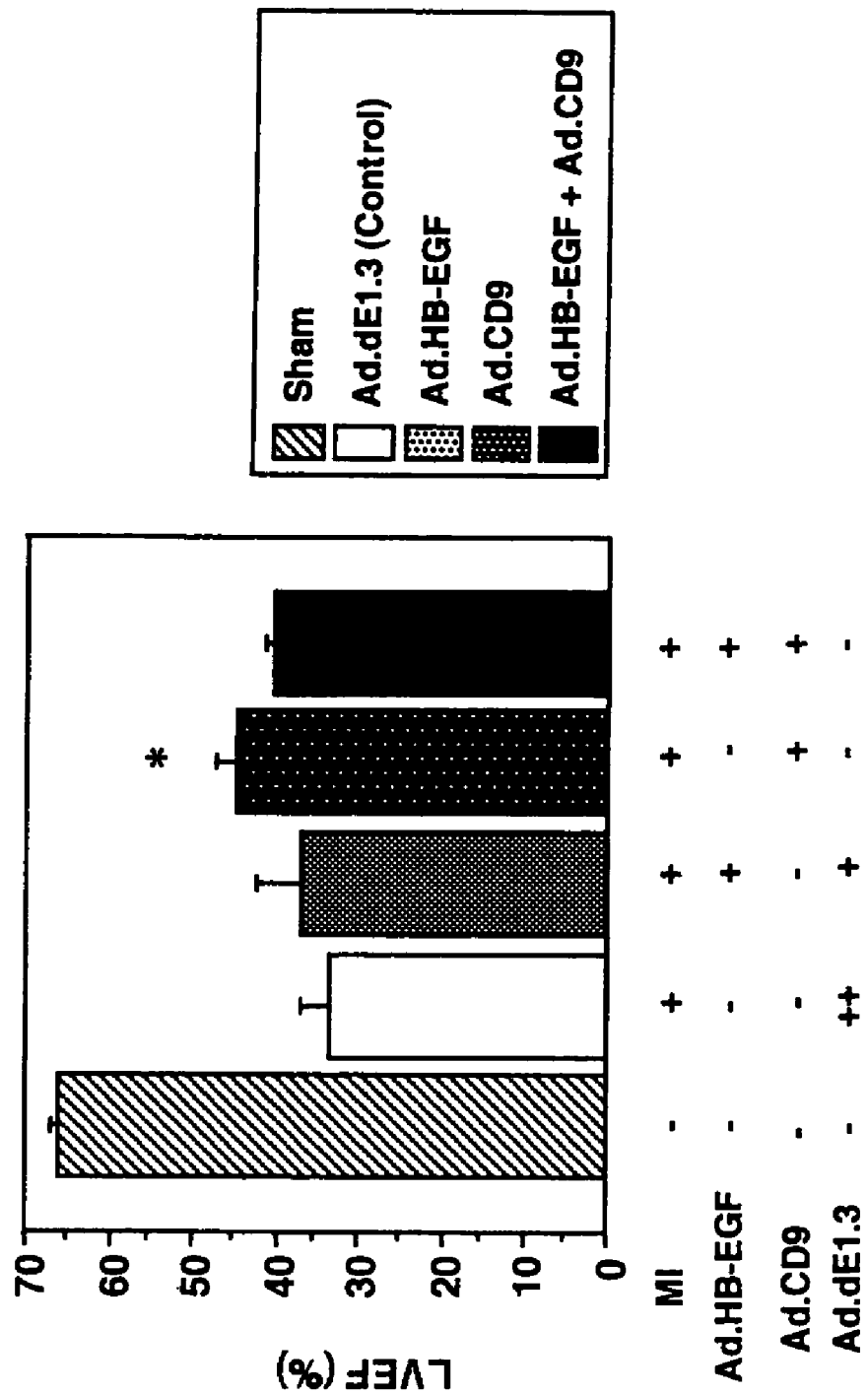
FIG. 13 shows a graph showing LVEF of echocardiography of adult mice 1-week after myocardial infarction. In this figure, sham represents a normal mouse not revealing myocardial infarction, and MI represents myocardial infarction (also in the following FIGS. 14 to 23).
Figure 14:
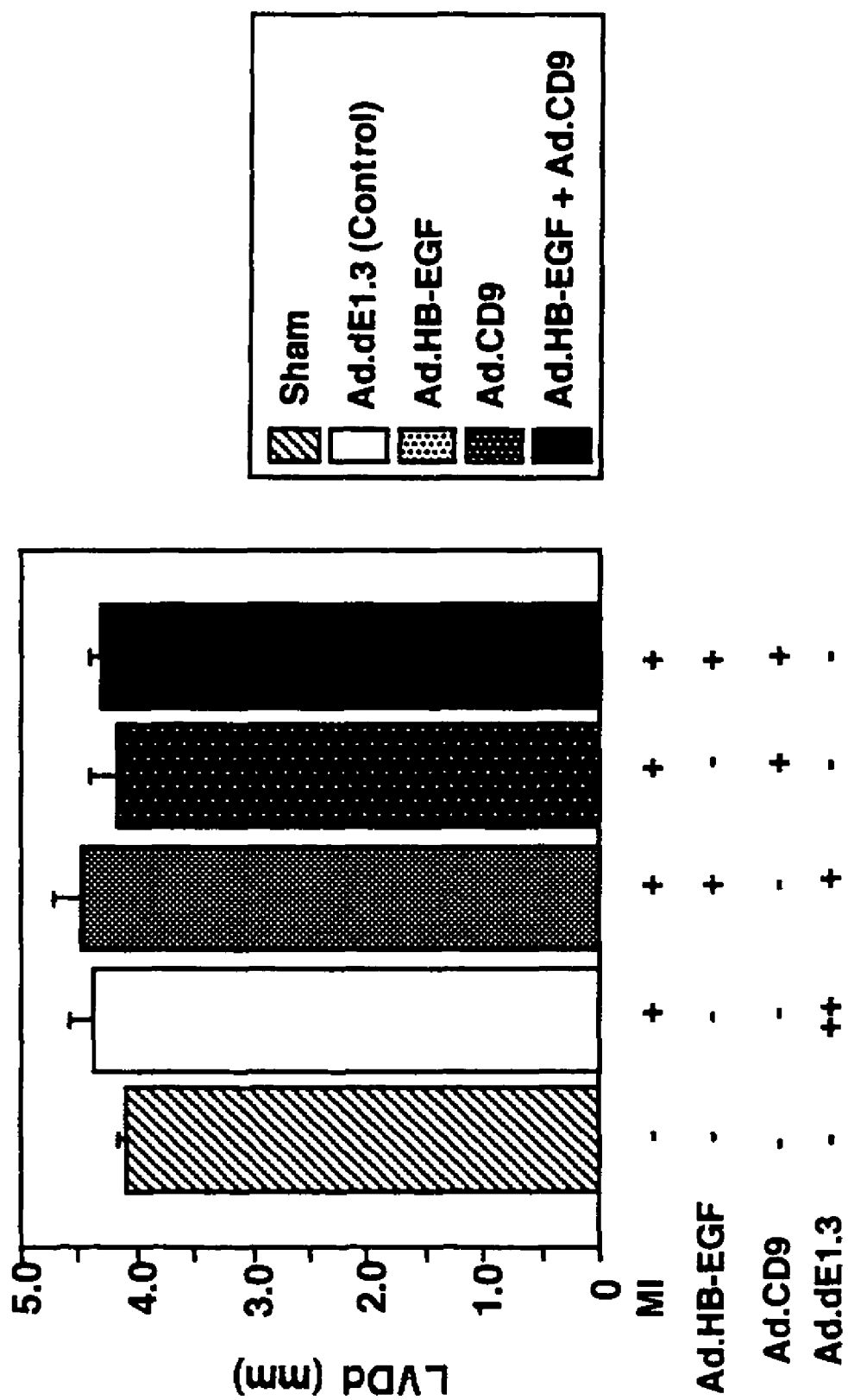
FIG. 14 shows a graph showing LVDd of echocardiography of adult mice 1-week after myocardial infarction.
Figure 15:
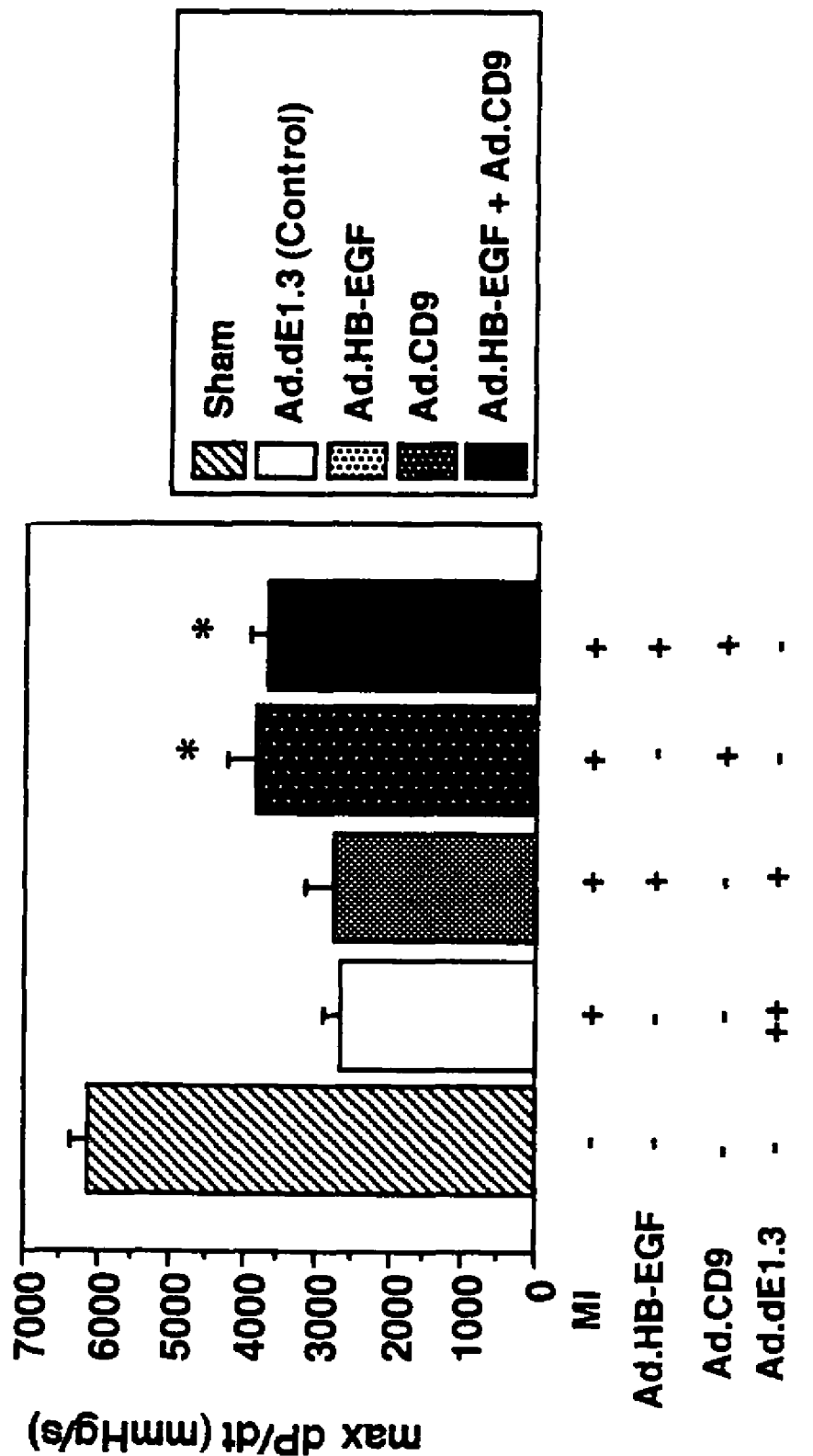
FIG. 15 shows a graph showing +dp/dt by a catheter in adult mice 1-week after myocardial infarction.
Figure 16:
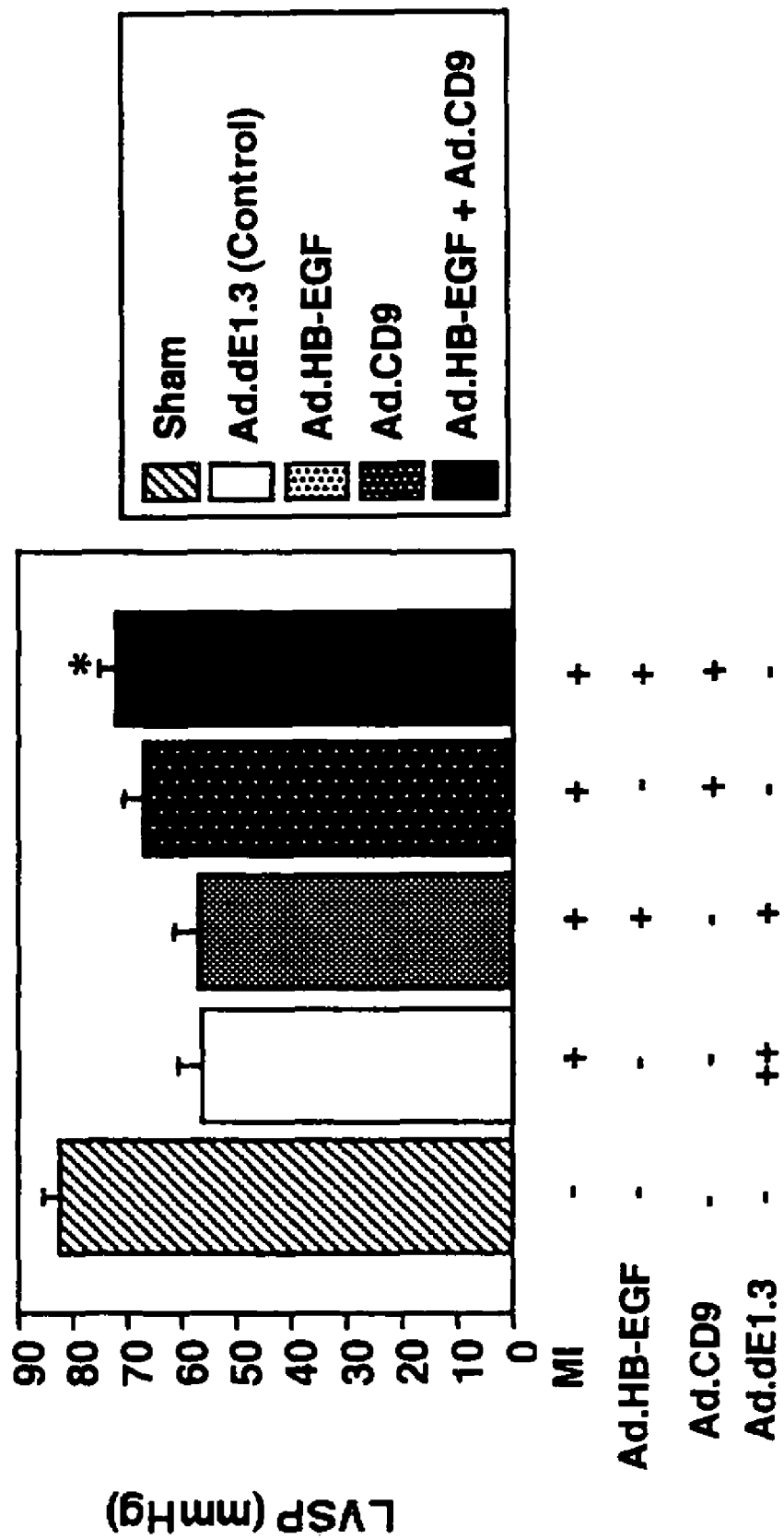
FIG. 16 shows a graph showing LVSP by a catheter in adult mice 1-week after myocardial infarction.
Figure 17:
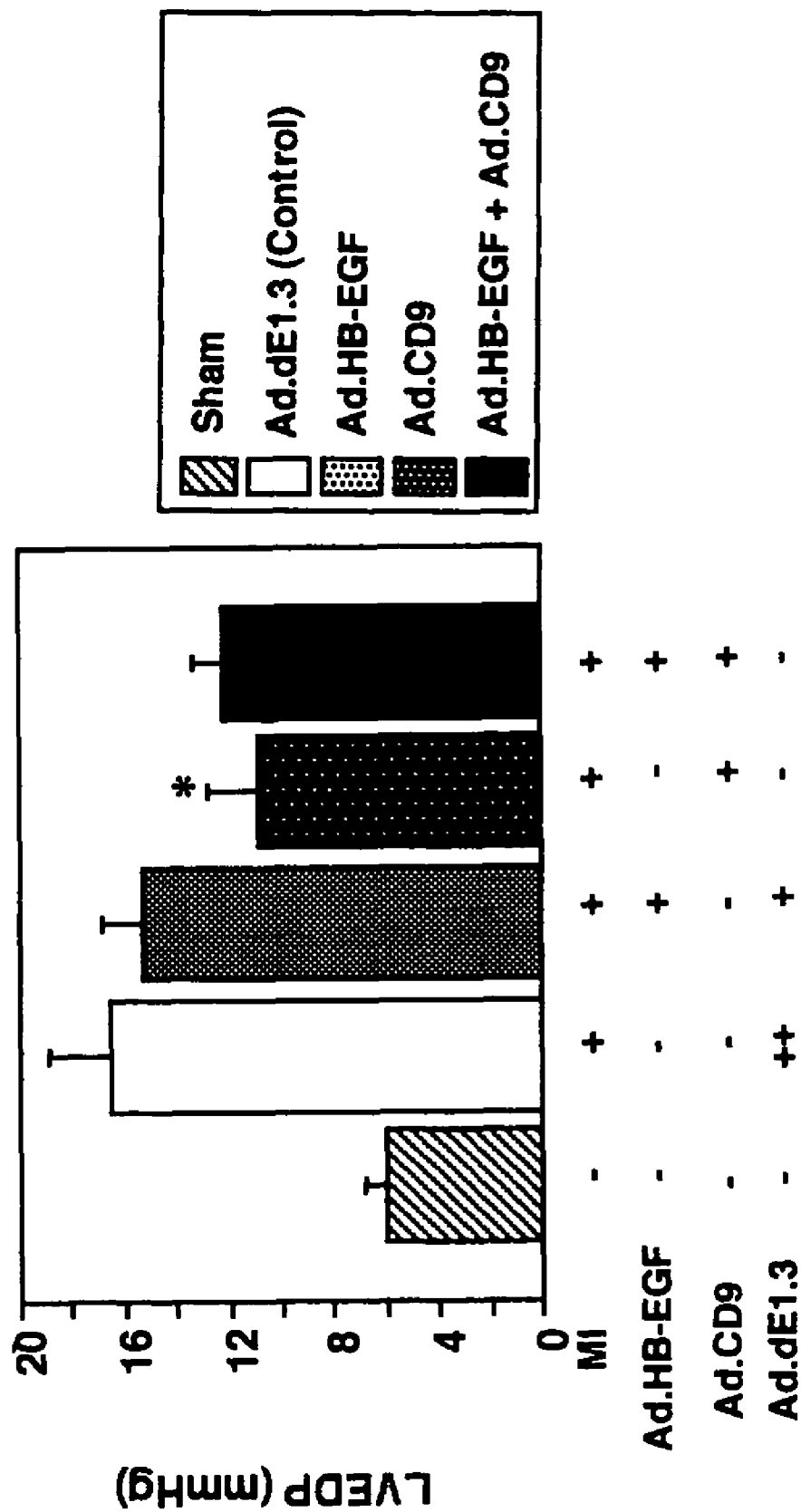
FIG. 17 shows a graph showing LVEDP by a catheter in adult mice 1-week after myocardial infarction.

Results of measurement of the cardiac function by echocardiography and a catheter of a model one week after myocardial infarction produced for investigating a reason for 80% death of the HB-EGF+dE 1.3 group in an acute phase within 2 weeks are as described below. The cardiac function of the CD9 gene-transferred group was significantly excellent as compared with the control group and the HB-EGF gene-transferred group (*p<0.05 vs control), in left ventricular ejection fraction (LVEF)(see, FIG. 13) in cardiac function evaluation by echocardiography, and in left ventricular maximum positivity dP/dt and left ventricular systolic pressure (LVSP) (FIG. 15 and FIG. 16) in invasive circulation kinetics evaluation by a catheter. As told that the size of left ventricle does not change in a short period of 1 week after myocardial infarction, no difference was observed in LVDd between the CD9 gene-transferred group and the control and HB-EGF gene-transferred groups (see FIG. 14). Similarly, a significant difference was not observed in a short period of time of 1 week after myocardial infarction, also regarding IVSt and PWt as an index for the thickness of a wall of left ventricle (not shown). Though LVEDP showed no significant differences, there was a tendency that it was lower in the CD9 gene-transferred group (see FIG. 17, *P<0.05 vs control).

These results show that gene-transferring of CD9 into heart suppresses cardiac hypertrophy and tachycardia, and is effective for prevention and improvement of heart diseases, thus, the drug of the present invention can also be applied in other heart failure models and the like.

EXAMPLE 7

MEASUREMENT OF ORGAN WEIGHT IN MYOCARDIAL INFARCTION ANIMAL MODEL

Figure 18:
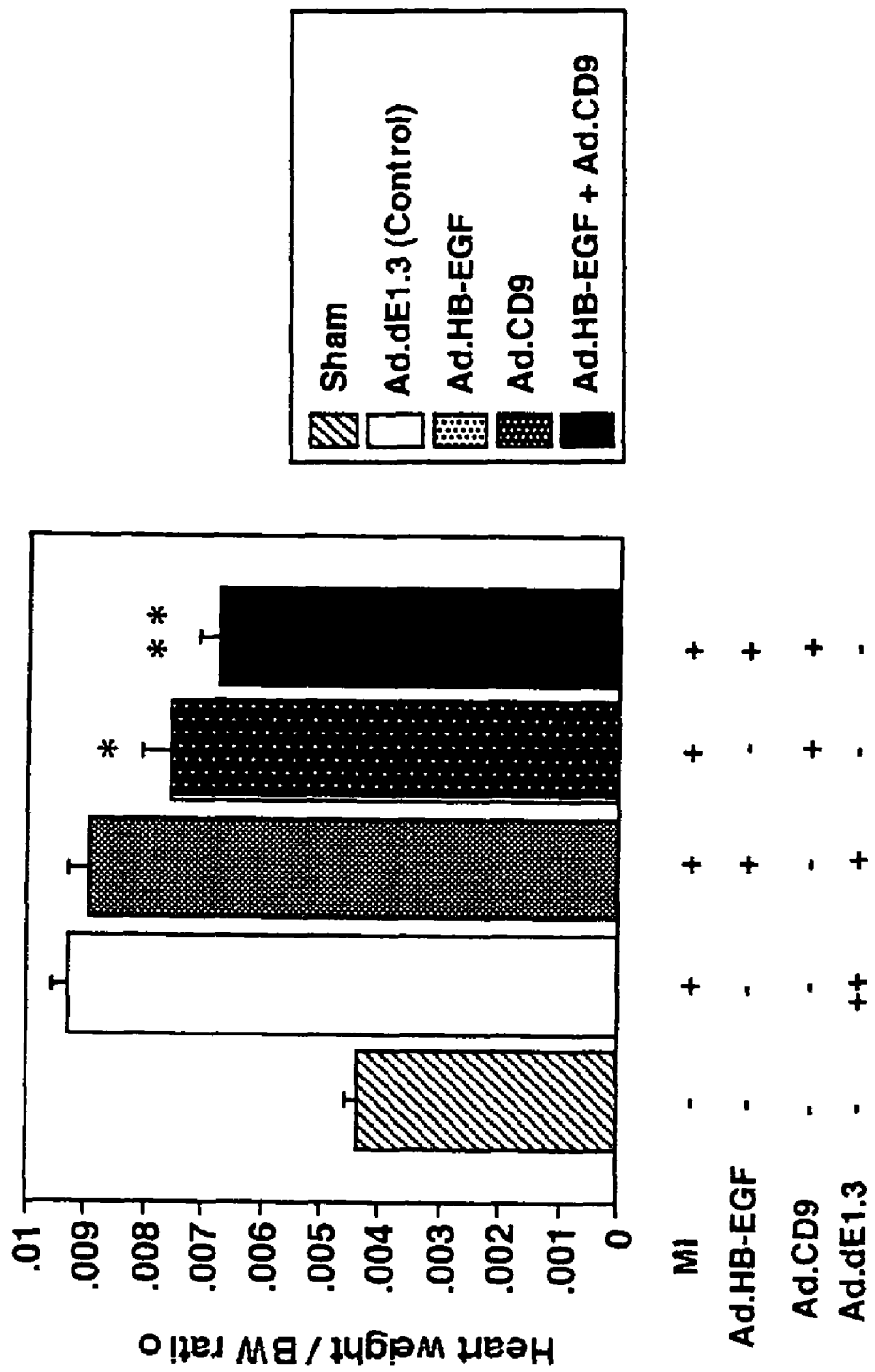
FIG. 18 shows a graph showing heart weight after correction of the body weight of adult mice 1-week after myocardial infarction.
Figure 19:
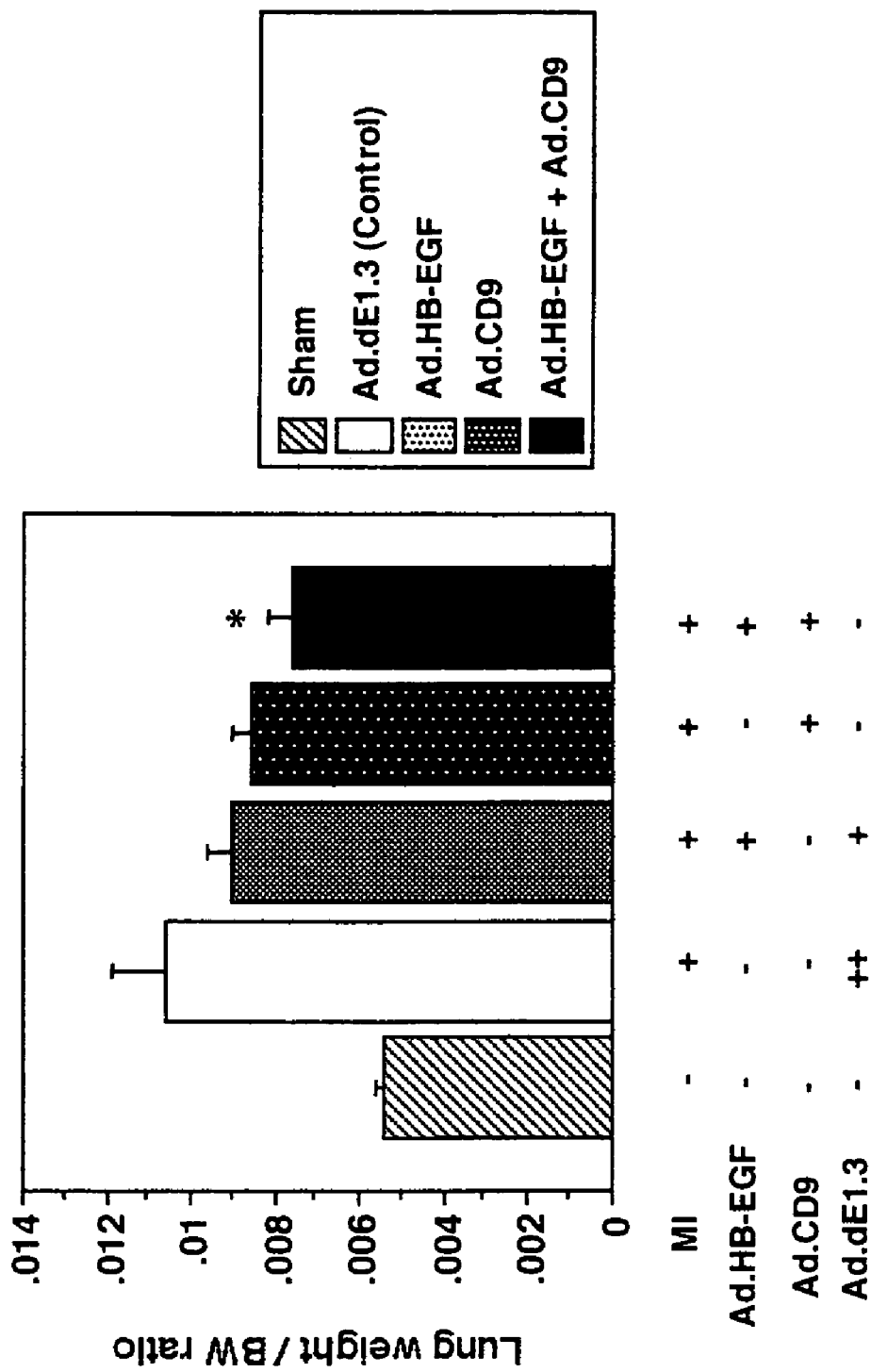
FIG. 19 shows lung weight after correction of the body weight of adult mice 1-week after myocardial infarction.

Mice of 1 week or more after myocardial infarction formation were tenderly sacrificed in all the groups. The body weights of mice after sacrificing were measured, and the weight of heart and the weight of lung were divided. by its body weight, and the weight of heart and the weight of lung were corrected. Increase in the weight of heart means excess hypertrophy and dilation of heart, indicating deterioration of the cardiac function such as heart failure and the like. Increase in the weight of lung means hemostasis of lung, indicating pulmonary edema, namely, heart failure. As a result, as shown in FIG. 18 and FIG. 19, the CD9 transferred group shows significant suppression of the organ weight, indicating no heart failure condition (*p<0.05 vs control, **p<0.001 vs control).

EXAMPLE 8

MEASUREMENT OF MYOCARDIAL INFARCTION REGION AREA AND FIBERED AREA OF MYOCARDIAL INFARCTION ANIMAL MODEL

Mice of 1 week or more after myocardial infarction formation were tenderly sacrificed in all the groups. After sacrificing, heart was removed and sliced to obtain sections which were fixed by formalin treatment, then, the section was subjected to Masson trichrome staining as an index for fibering.

Figure 20:
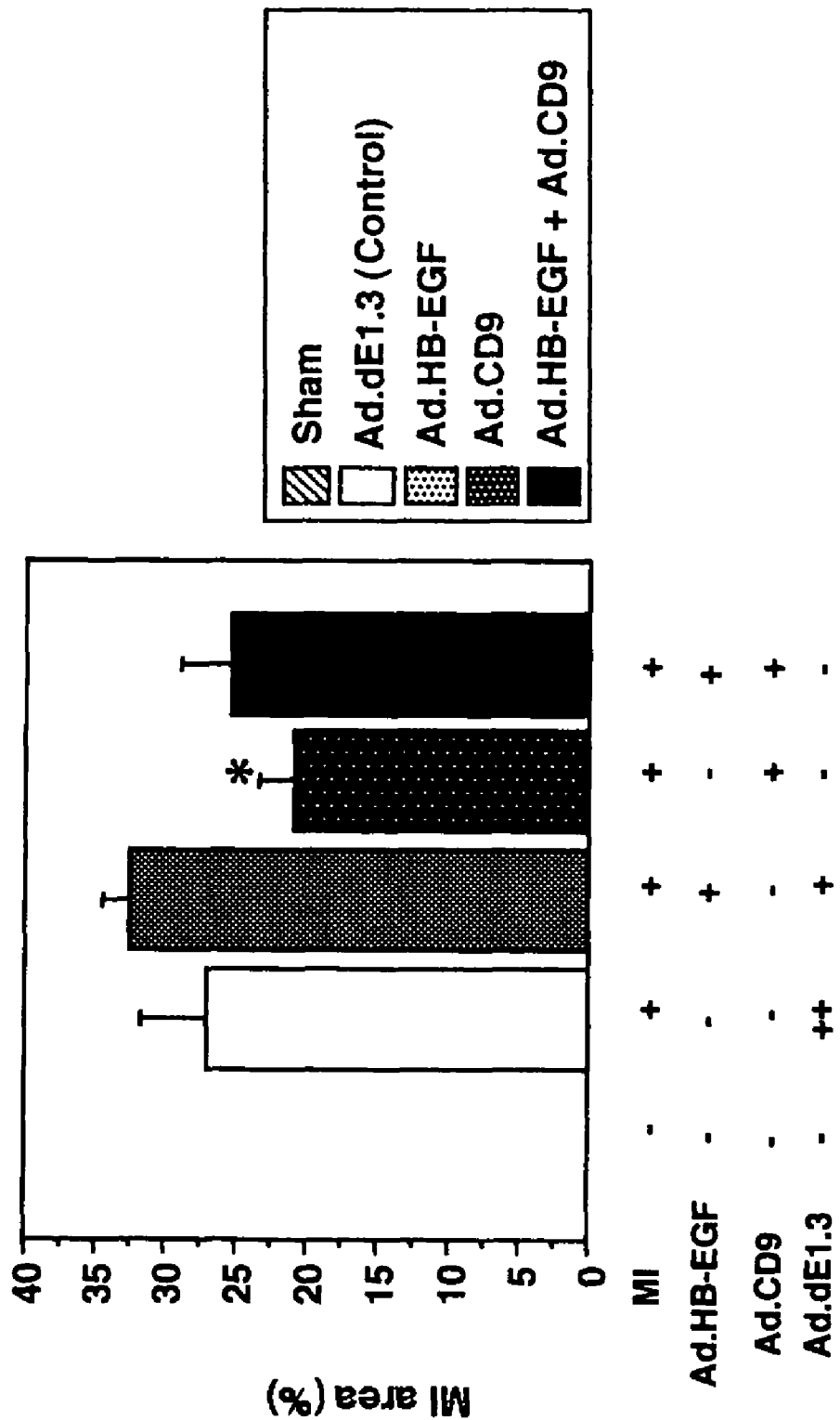
FIG. 20 shows a graph showing the area of a myocardial infarction region of adult mice 1-week after myocardial infarction.
Figure 21:
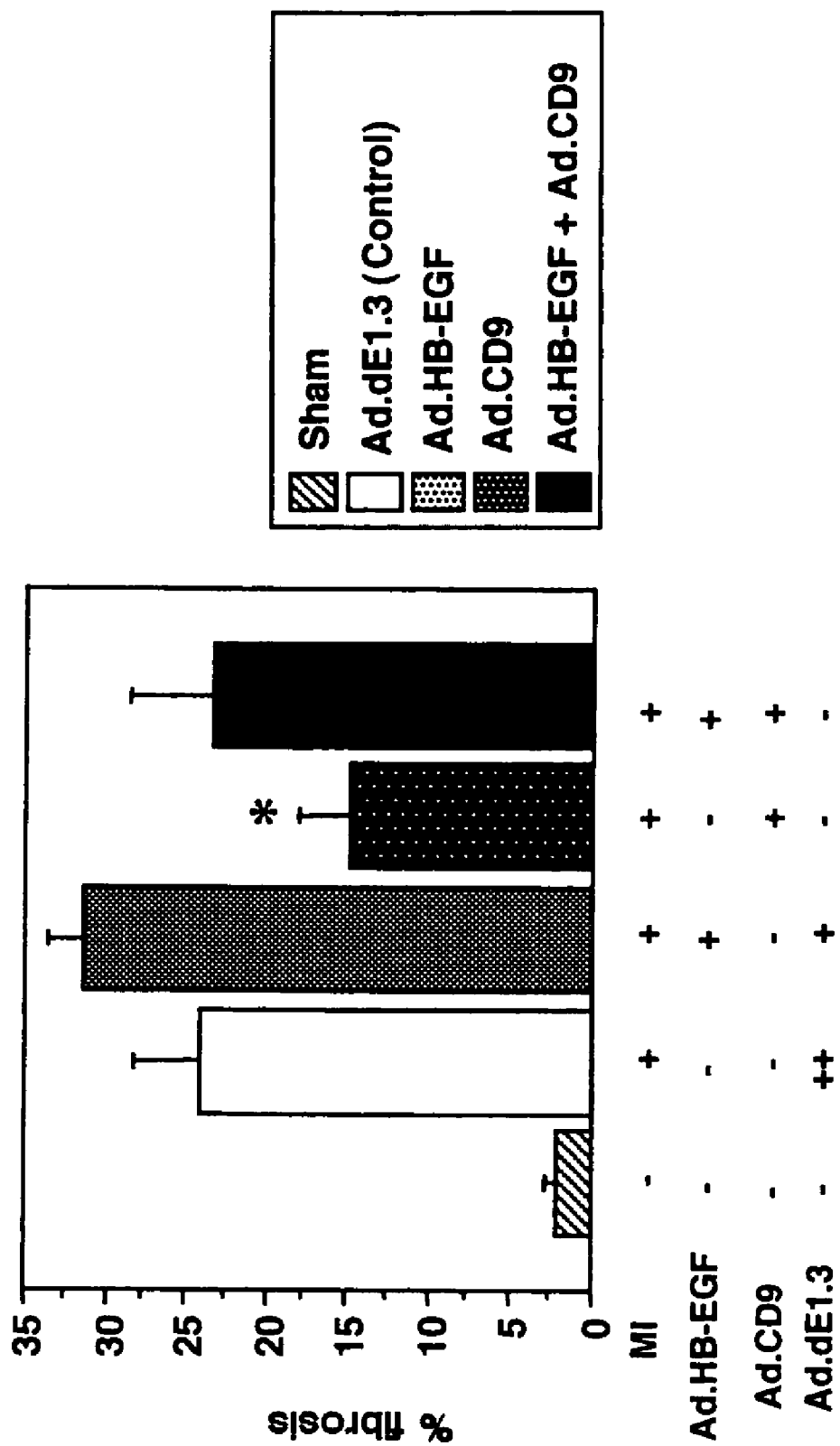
FIG. 21 shows a graph showing the fibered area of adult mice 1-week after myocardial infarction.

Regarding the myocardial infarction region area (MI area), the ratio of a heart necrosis part in the whole left ventricle was calculated. Regarding the fibered area, particularly the ratio of a positive part by Masson trichrome staining based on the area of all left ventricle sections was calculated. As a result, as shown in FIG. 20 and FIG. 21, the CD9 transferred group showed a significant decrease, revealing a therapeutic effect, in both the myocardial infarction region area (MI area) and the fibered area (*p<0.05 vs control).

EXAMPLE 9

IMMUNOHISTOLOGICAL INVESTIGATION OF MYOCARDIAL INFARCTION REGION IN MYOCARDIAL INFARCTION ANIMAL MODEL

Figure 22:
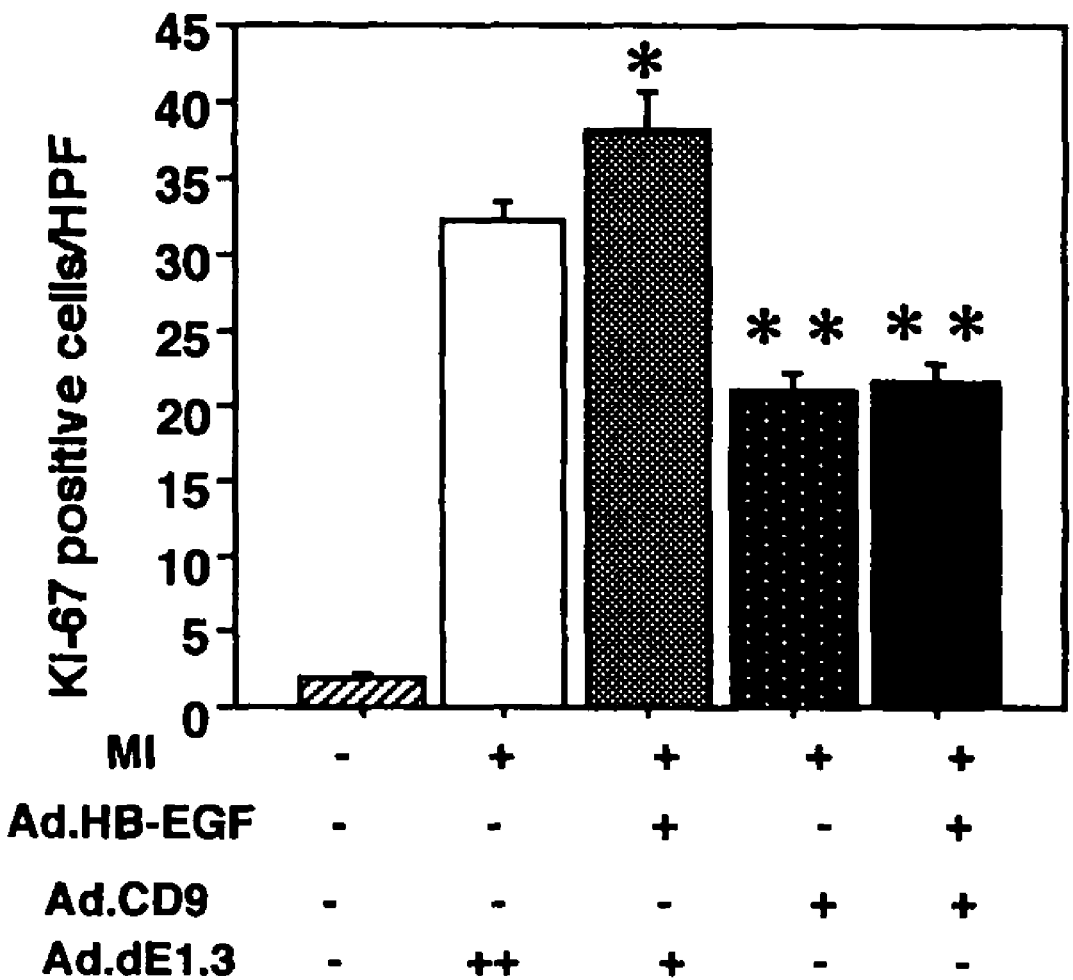
FIG. 22 shows a graph showing grown cells of cardiac muscle of adult mice 1-week after myocardial infarction.
Figure 23:
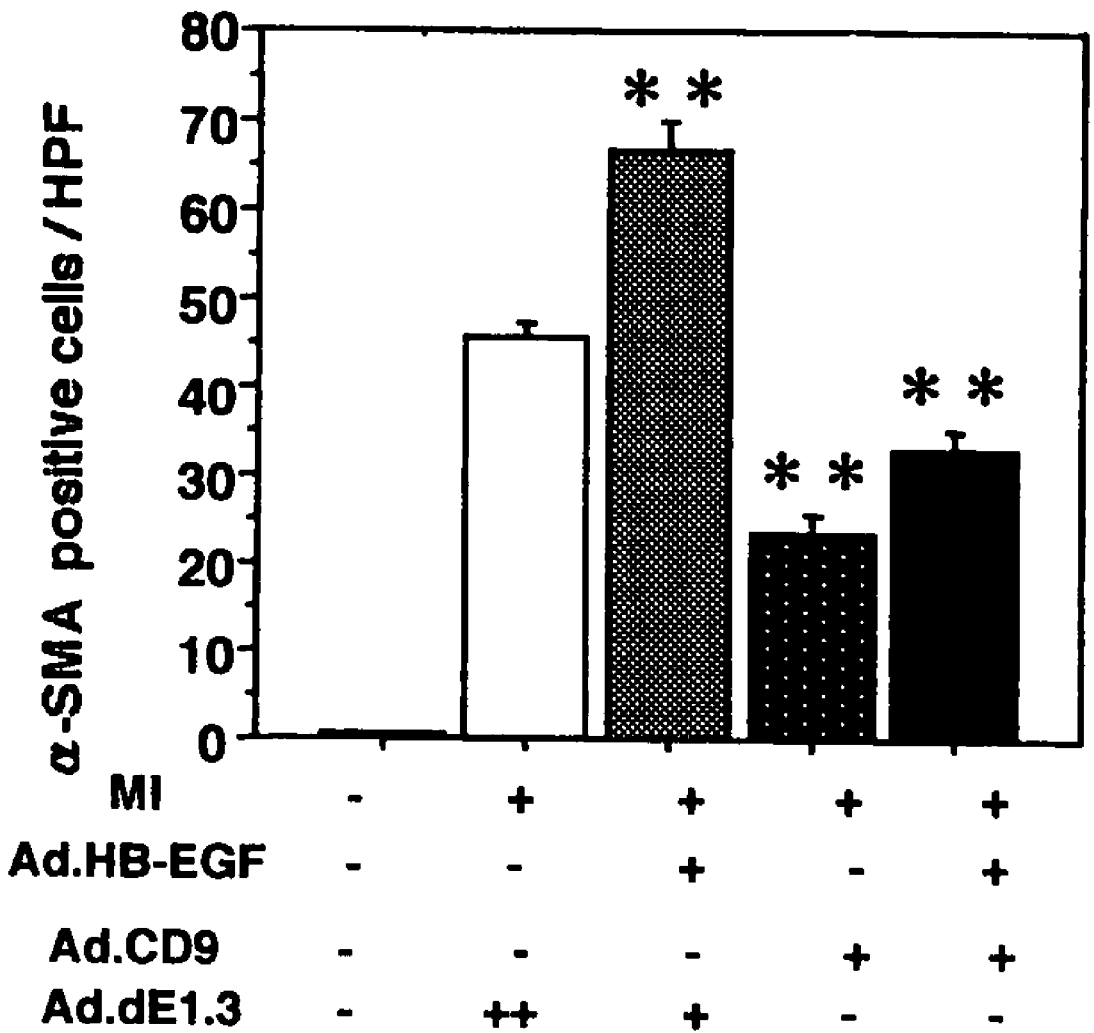
FIG. 23 shows a graph showing myofibroblasts of cardiac muscle of adult mice 1-week after myocardial infarction.

Mice of 1 week or more after myocardial infarction formation were tenderly sacrificed in all the groups. After sacrificing, heart was removed and fixed by formalin treatment, then, embedded in paraffin, and sliced. The heart slices were stained using a monoclonal antibody to a Ki-67 antigen (clone: MIB-1, Dako Cytomation, catalogue No. M7240, antibody dilution 25-fold) as an index for grown cells and DAKO EPOS/HRP (Enhanced Polymer One-step Staining/peroxidase) kit (clone: 1A4, Dako Cytomation, catalogue No. U7033) of a monoclonal antibody to anti-smooth muscle fiber actin (α-smooth muscle actin (SMA)) as an index for myofibroblast. Staining positive cells were observed using a microscope, and positive cells were counted per unit visual field in 10 visual fields for 1 sample in every group by observation at a high magnification of 200-fold (High Power Field (HPF)), and averaged and graphed. As a result, as shown in FIG. 22 and FIG. 23, the CD9 transferred group showed a significant decrease in both the grown cell and myofibroblast, clarifying that CD9 suppresses irregular and excess repair of the grown cell, suppression of granulation and proliferation of a myofibroblast (*p<0.05 vs control, **p<0.001 vs control)

INDUSTRIAL APPLICABILITY

The drug of the present invention is used for gene therapy, and can prevent or treat radically heart diseases, particularly, heart diseases associated with cardiac hypertrophy and tachycardia by transferring a CD9 gene into heart. The prevention or treatment method for the present invention can radically prevent or treat heart diseases by allowing a CD9 gene to express in heart.

The present invention is not limited to the above-mentioned examples providing it is included in a substantial range of the invention.

The invention claimed is:

1. A method for suppressing cardiac hypertrophy or cardiac tachycardia in a subject having a heart disease, comprising administering directly to a cardiac muscle in the heart of the subject an expression vector containing a sequence encoding a CD9 protein;

wherein cardiac hypertrophy or cardiac tachycardia is suppressed in the subject.

2. The method according to claim 1, wherein the heart disease is an ischemic heart disease.

3. The method according to claim 2, wherein the ischemic heart disease is myocardial infarction.

4. The method according to claim 1, wherein cardiac hypertrophy or tachycardia is caused by at least one of heparin binding epidermal growth factor (HB-EGF), hepatocyte growth factor (HGF) or angiotensin 2.

5. The method according to claim 1, wherein the expression vector is a viral vector or a non-viral vector.

6. The method according to claim 5, wherein the viral vector is an adenovirus, an adeno-associated virus, a retrovirus, a herpesvirus, a herpes simplex virus, a lentivirus, a Sendai virus, a poxvirus, a poliovirus, a symbis virus, or a vaccinia virus.

7. The method according to claim 6, wherein the expression vector is adenovirus.

8. The method according to claim 7, wherein the heart disease is an ischemic heart disease.

9. The method according to claim 8, wherein the ischemic heart disease is myocardial infarction.

10. The method according to claim 5, wherein the non-viral vector is a cationic liposome, a membrane-fusing liposome, or a cationic polymer.

11. The method according to claim 10, wherein the heart disease is an ischemic heart disease.

12. The method according to claim 11, wherein the ischemic heart disease is myocardial infarction.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence : PCR primer

<400> SEQUENCE: 1
ccgtgatgct gaagctcttt                                          20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence : PCR primer

<400> SEQUENCE: 2
ccaagactgt agtgtggtca t                                        21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence : PCR primer

<400> SEQUENCE: 3
agcaagtgca tcaaatacc                                           19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence : PCR primer
```

-continued

```
<400> SEQUENCE: 4
aatcacctca tccttgtgg                                                  19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence : PCR primer

<400> SEQUENCE: 5
acaactgtga agtggtcct                                                  19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence : PCR primer

<400> SEQUENCE: 6
ttcctgtaag ttccgcat                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence : PCR primer

<400> SEQUENCE: 7
agctggtgac acagctta                                                   18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence : PCR primer

<400> SEQUENCE: 8
tggttgggac tcttgac                                                    17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence : PCR primer

<400> SEQUENCE: 9
gacctagacc tagactt                                                    17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence : PCR primer

<400> SEQUENCE: 10
tctgatgact ctgatgc                                                    17
```

```
<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence : PCR primer

<400> SEQUENCE: 11
catctacaca tccagaaca                                                  19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence : PCR primer

<400> SEQUENCE: 12
aaacatctca gccgttgca                                                  19
```